United States Patent [19]
Hajduk

[11] Patent Number: 6,157,449
[45] Date of Patent: Dec. 5, 2000

[54] DEPOLARIZED LIGHT SCATTERING ARRAY APPARATUS AND METHOD OF USING SAME

[75] Inventor: Damian A. Hajduk, San Jose, Calif.

[73] Assignee: Symyx Technologies, Santa Clara, Calif.

[21] Appl. No.: 09/174,986

[22] Filed: Oct. 19, 1998

[51] Int. Cl.[7] ....................................... G01J 4/00
[52] U.S. Cl. ........................ 356/367; 356/364; 356/365; 356/345; 356/351
[58] Field of Search .................... 356/367, 365, 356/364, 345, 346, 351, 445, 368

[56] References Cited

U.S. PATENT DOCUMENTS

| | | | |
|---|---|---|---|
| 5,257,092 | 10/1993 | Noguchi et al. | 356/367 |
| 5,694,205 | 12/1997 | Gualtieri et al. | 356/365 |
| 5,788,632 | 8/1998 | Pezzaniti et al. | 356/368 |
| 6,031,614 | 2/2000 | Michaelis et al. | 356/369 |

FOREIGN PATENT DOCUMENTS

| | | |
|---|---|---|
| PCT/US97/18521 | 10/1997 | WIPO . |

*Primary Examiner*—Frank G. Font
*Assistant Examiner*—Roy M. Punnoose

[57] ABSTRACT

A method and apparatus for characterizing and scanning an array of material samples in a combinatorial library in parallel is disclosed. The apparatus includes a sample block having a plurality of regions for containing the material samples, a polarized light source to illuminate the materials, an analyzer having a polarization direction oriented 90° relative to the polarization direction of the polarized light source so as to filter out light intensities having the same polarization direction as the incident light beams from the light source after illuminating the material samples, and a detector for analyzing changes in the intensity of the light beams. In one aspect, the light source in combination with a polarizer, includes a plurality of light beams to simultaneously illuminate the entire array of materials with linearly polarized light such that the characterization can be performed quickly. In another aspect, the materials in the sample block are subjected to different environmental conditions wherein the detector analyzes the array as a function of those environmental conditions.

102 Claims, 15 Drawing Sheets

DEPOLARIZED LIGHT SCATTERING ARRAY APPARATUS AND METHOD OF USING SAME

BACKGROUND

1. Technical Field

The present invention relates to a method and apparatus for rapidly screening and characterizing an array of materials. More particularly, this invention is directed to an optical technique for the parallel screening and characterizing of different materials in a combinatorial library.

2. Discussion

Combinatorial materials science refers generally to methods for creating a collection of chemically diverse materials or compounds and to methods for rapidly testing or screening such collections, commonly known as libraries, for desirable performance characteristics and properties. In recent years, the advent of combinatorial chemistry has revolutionized the process of drug discovery (see for example 29 *Acc. Chem. Res.* 1–170 (1996); 97 *Chem. Rev.* 349–509 (1997); S. Borman, *Chem. Eng. News* 43–62 (Feb. 24, 1997); A. M. Thayer, *Chem. Eng. News* 57–64 (Feb. 12, 1996); N. Terret, 1 *Drug Discovery Today* 402 (1996)). Researchers have also used combinatorial strategies in the discovery and optimization of materials, such as superconductors, zeolites, magnetic materials, phosphors, catalysts, thermoelectric materials, high and low dielectric materials and the like.

Although new and useful materials can be developed in less time using combinatorial methods, further efficiency gains can be achieved by improving the speed and efficiency of library screening. Once a combinatorial library is created, there looms the daunting task of identifying a handful of promising compounds or materials out of a combinatorial library comprising hundreds, thousands or perhaps millions of compounds or materials. While the use of combinatorial methods in synthesizing candidate compounds or materials speeds up the discovery process, testing the individual compounds or materials can consume a significant amount of time and resources.

Known analytical techniques are often unsuitable for screening combinatorial libraries because of poor sensitivities, slow response and the inherently serial nature of most instrumentation. The latter two difficulties can be overcome by adopting parallel measurement techniques, in which the same characterization method is applied to all elements in the library simultaneously. However, the ease with which this can be accomplished is strongly dependent on the specific nature of the technique utilized. Optically based methods possess a clear advantage in this regard in that parallel data collection and analysis is easily accomplished using preexisting imaging and image processing technologies. The optical characteristics of a compound or material reflect the electronic properties of the constituent molecules as well as the arrangement of these molecules in space, making it possible to detect changes in physical or chemical structure through optical means. One known application of such a method has been applied to screening selected characteristics of materials as a function of applied voltage (described in co-pending U.S. patent application Ser. No. 08/947,085 "Optical Systems and Methods for Rapid Screening of Libraries of Different Materials", published as WO 98/15805, which is incorporated herein by reference).

However, there exists a need for other apparatuses and methods for rapidly screening and characterizing, in parallel, the optical and physical properties of an array of compounds or materials.

SUMMARY

In accordance with the present invention, there is provided an apparatus for screening an array of at least partially transparent material samples in a combinatorial library, wherein the material samples exhibit changes in birefringence as a function of environmental conditions. The apparatus includes a sample block having a plurality of regions therein for receiving the library members. The term sample block is not meant to place any structural limitations (e.g. size or shape) on the invention. The apparatus also includes a light source that provides at least one light beam light that is polarized and directed toward the regions, an analyzer for filtering out light having the same polarization as the incident light beam after it passes through the regions, and a detector for analyzing changes in the intensity of the light beams due to the optical characteristics of the library members. The sample block, light source, analyzer and detector are all arranged in series.

Preferably, the sample block receives vials of the material samples within the regions formed therein. The vials that receive the library members can be constructed from any material or combination of materials which are at least partially transparent to the light emitted by the source. Suitable materials include glass, quartz, and transparent plastic sheets which are generally free of residual stresses. These vials should be nonbirefringent, in that, they should not alter the polarization characteristics of light which passes through them.

In accordance with one aspect of the invention, the light source preferably includes a plurality of lights, such as light emitting diodes (LEDs), that are all directed toward the regions simultaneously such that the entire array of material samples may be illuminated at once. A polarizer, such as a commercially available polarizing filter or polarizing mirror, is placed between the light source and the regions to polarize the light before it passes through the vials and material samples in the library. The polarized light beams are then collimated, preferably by passing the light beams through a separate collimator plate, to reduce stray light. Passage through the material sample alters the polarization of the light in a manner determined by the structural characteristics of the material sample. Next, the light beams are passed through a second polarizer, i.e., an analyzer, wherein the second polarizer has a preferred polarization direction oriented at 90° relative to the first polarizer. The analyzer serves to filter the light beams, only transmitting that fraction of the radiation which has a specific linear polarization.

In accordance with another aspect of the invention, the detector includes a fiber optic assembly and a charged coupled device (CCD) camera to capture readings of the light intensity transmitted through the material samples. A first fiber optic plate is positioned above the second polarizer and a second fiber optic plate is placed above the first fiber optic plate. A bundle of fiber optics is placed between the plates with the ends of the fibers extending through holes in both plates. Light transmitted through the second polarizer is captured by the fiber ends extending through the first plate and transmitted through the fibers to emerge at the second plate. The fibers in the bundle are arranged in a tapered configuration so as to reduce the dimensions of the area over which the light is distributed from the array of samples to a size more easily imaged by the CCD camera.

In accordance with another aspect of the invention, the apparatus may also include a temperature controlled block. The sample block holding the vials of material samples is disposed within the temperature controlled block such that intensity readings of the material samples may be evaluated as a function of temperature. The apparatus may further include a substantially gas-tight environmental chamber. The sample block holding the vials of material samples is mounted within the substantially gas-tight environmental chamber and at least one gas is directed into the chamber so as to subject the material samples to pressure, wherein intensity readings of the material samples may be evaluated as a function of pressure. Alternatively, the substantially gas-tight environmental chamber may be subject to a continuous mixture of two or more gases such that intensity reading of the material samples may be evaluated as a function of the gas mixture composition.

In accordance with another aspect of the invention, the sample block may further include an array of electrode pairs, wherein a separate electrode pair is associated with each region. The electrode pairs are arranged in an opposing manner with the region containing the materials disposed there between. A power supply is connected in series with the electrode pairs such that when voltage is applied to the pairs, an electric field is generated across each material sample. The intensity readings of the material samples may then be evaluated as a function of applied voltage.

In accordance with another aspect of the invention, the sample block may further include pairs of electromagnetic devices, wherein a separate electromagnetic device pair is associated with one region. The pairs of electromagnetic devices are arranged in an opposing manner with the region disposed therebetween. A power supply is connected in series with the pairs of electromagnetic devices such that when voltage is applied, a magnetic field is generated across each material sample. The intensity readings of the material samples may then be evaluated as a function of magnetic field strength.

In accordance with another aspect of the invention, there is provided a method of characterizing an array of material samples of a combinatorial library comprising the steps of providing an array of material samples in transparent sample blocks, e.g. in vials, illuminating at least one material in the array with a beam of polarized light that passes through the vials, filtering out intensity of the polarized light beam that has the same polarization direction as the incident light beam by passing the polarized light beam through an analyzer having a polarization direction oriented at a predetermined angle, (e.g. without limitation, 90° with respect to the direction of the polarized light beam), detecting changes in the intensity of the polarized light beam due to the optical characteristics of the material sample and determining characteristics of at least one material based on the detected changes in the intensity values. In the preferred method, a plurality of polarized light beams are provided such that the entire array of material samples is illuminated simultaneously.

In accordance with another aspect of the invention, the method may further include determining characteristics of the material samples as a function of various environmental conditions. In one embodiment, the temperature of the material samples is varied such that the detecting and determining steps are performed as a function of temperature. In another embodiment the materials are subject to pressure such that the detecting and determining step are performed as a function of pressure. The material sample may also be continuously subjected to a mixture of gases such that the detecting step may be done as a function of gas composition. Further, the method also may include generating an electric field across each material samples such that the detecting and determining step are performed as a function of applied voltage. In yet another embodiment, the method may include generating a magnetic field across each material sample such that the detecting and determining step are performed as a function of magnetic field strength.

BRIEF DESCRIPTION OF THE DRAWINGS

FIG. 2b is a top view of the sample block of FIG. 2a.

FIG. 4b is a side view of the collimator block of FIG. 4a.

FIG. 7b is a side view of the temperature controlled block of FIG. 7a.

FIG. 8b is a side view of the alternative embodiment of the temperature controlled block of FIG. 8a.

FIGS. 13–16 are negative images of the array of materials captured by a CDD camera at differing temperature intervals.

DETAILED DESCRIPTION OF THE PREFERRED EMBODIMENT

Figure 1:
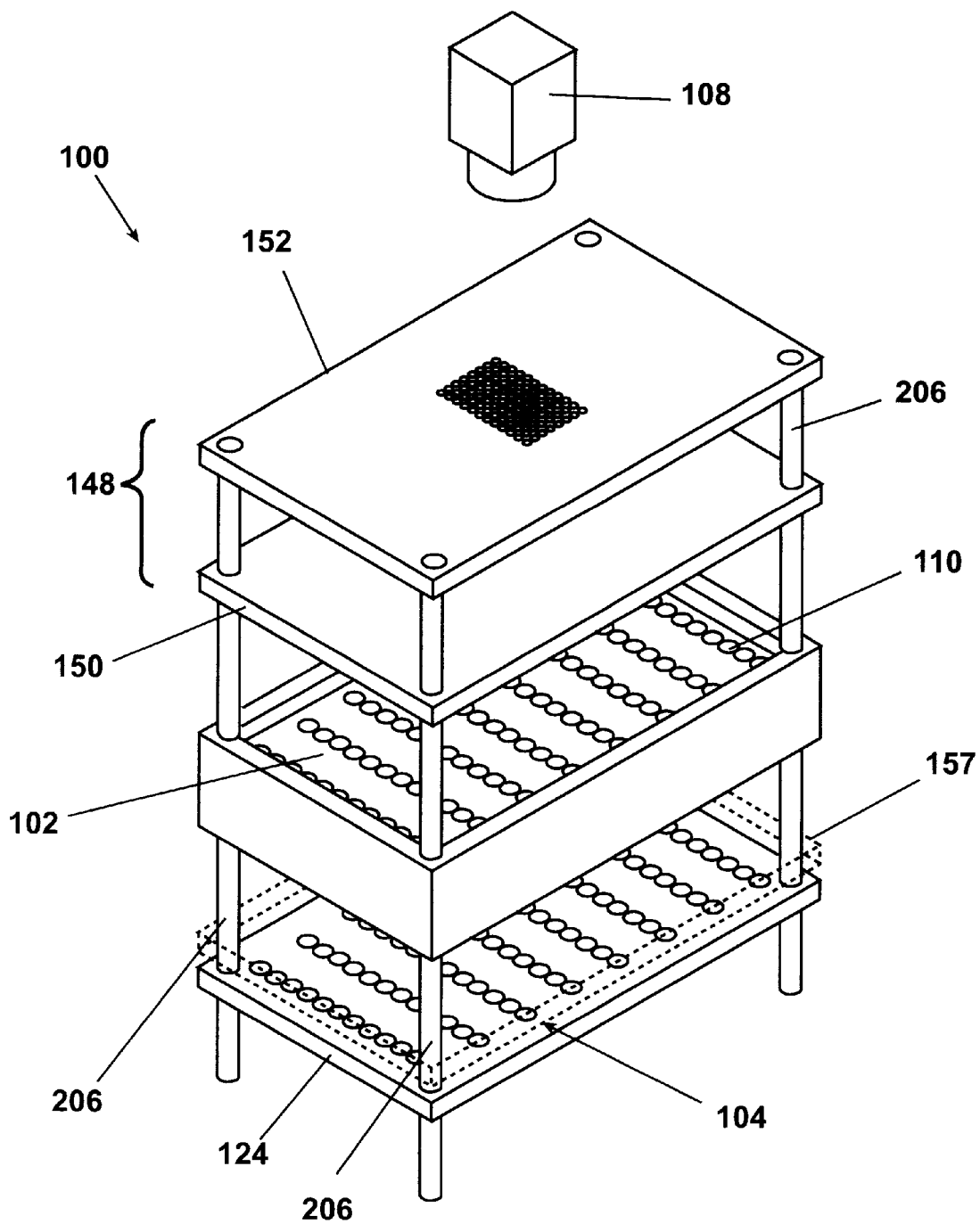
FIG. 1 is a schematic drawing of an apparatus for rapidly screening members of a combinatorial library in accordance with the present invention.

Overview of a Depolarized Light Scattering Array Apparatus

The present invention provides an apparatus and method for screening an array of material samples in a combinatorial library. Rapid screening is achieved by passing polarized light first through the compounds or materials being characterized and then through a polarizing filter, and measuring changes in the intensity of the transmitted light as a function of time and/or environmental conditions. The apparatus of the present invention allows for screening to be done simultaneously, in parallel, for two or more library material samples or to be carried out in a rapid serial manner or a combination of the two. Among other benefits, changes in the intensity of the transmitted light indicate changes in the optical characteristics of a material. The changes are generally associated with one or more structural transformations such as the melting, formation, or annealing of crystallites;

the relaxation of stress-induced deformations; molecular alignment or randomization; or transitions between different crystalline or liquid crystalline arrangements of the molecules of a material. Such transformations may be driven by changes in material composition, as when volatile components of a given compound are driven off by heating above a certain temperature; by changes in environmental conditions such as temperature, pressure, or local electric field strength; or by acceleration of kinetically constrained processes such as, without limitation, the relaxation of a mechanically stressed polymer film upon heating above its glass transition temperature. Thus, the present invention may be used to monitor structural, kinetic, and thermodynamic characteristics of an array of material samples, or to identify materials desirable for a specific application.

In principle, the number of material samples which can be measured in parallel is restricted by the number of independent measurement channels available. This can exceed 200,000 for inexpensive, commercially available CCD cameras. However, in practice, the number of material samples is limited to the number of samples which can be prepared in a reasonable amount of time for a single set of measurements, and by the physical dimensions of the device. Typical arrays contain between 10 and 1000 samples.

In materials where the transformations or relaxations of interest are slow (e,g, polymers), the minimum measurement time is typically set by the time required for the samples to achieve equilibrium at a given set of environmental conditions (temperature, pressure, etc.) Such values generally range from 5 to greater than 15 minutes, resulting in an effective throughput in the order of 60 samples/hr for ten measurements of an array of 100 elements. In the absence of such kinetic retardation, the measurement time is frequently set by the speed at which sufficiently large environmental changes can be produced. Typical thermal ramp rates range from 0.5 to 10° C./min; measurement at 1 degree intervals yields throughputs on the order of 1200 samples/hr. Comparable performance can be obtained when varying pressure or gas composition. Although local electric and magnetic fields can be varied at much higher frequencies, measurement will be limited in practice by the speed with which samples can be prepared and loaded into the apparatus, effectively constraining the sampling rate to less that 2000 samples/hr.

Figure 2A:
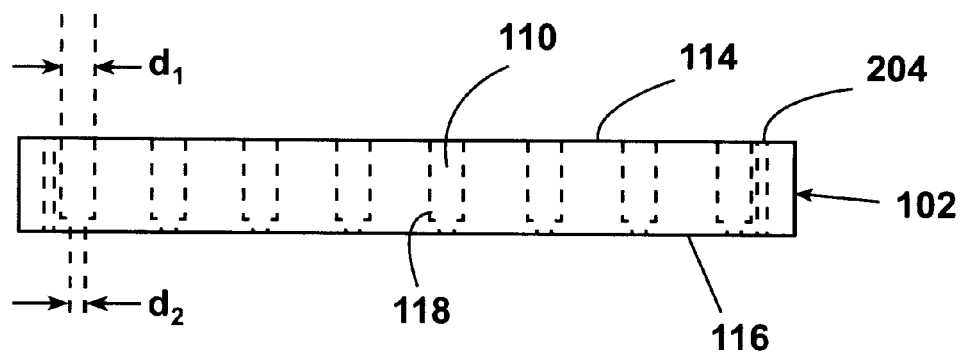
FIG. 2a is a side view of a sample block for holding the members of the combinatorial library.
Figure 2B:
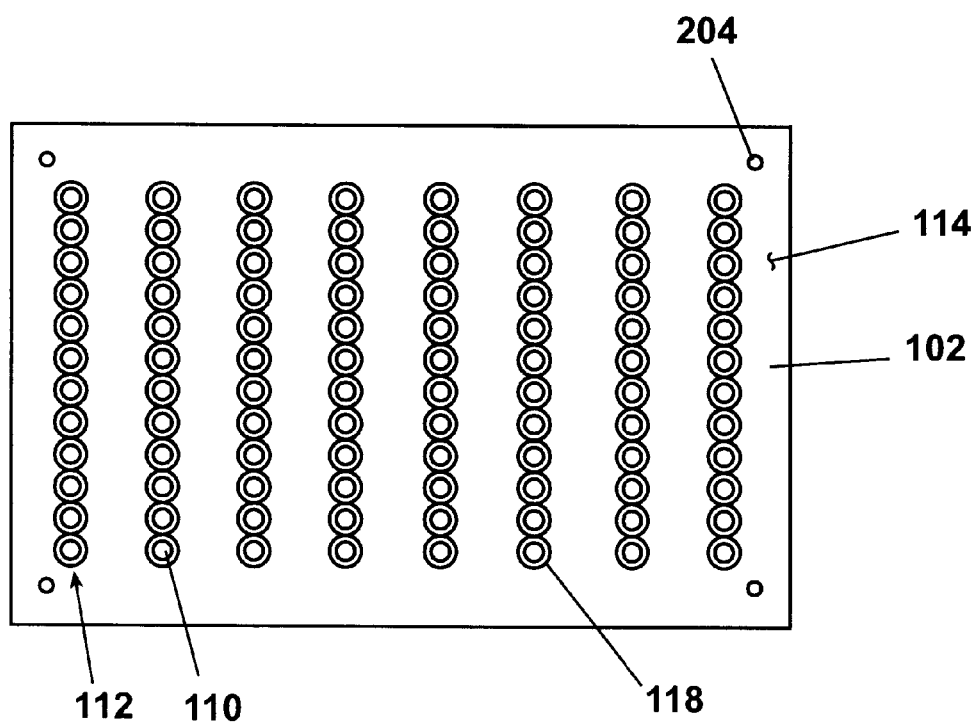

To perform such measurements describer above, FIG. 1 illustrates a first embodiment of an assembled depolarized light scattering apparatus 100 according to the present invention. Apparatus 100 includes a sample block 102 for receiving material samples for a combinatorial library, a light source 104, at least one polarizer (not shown in FIG. 1) and a detector 108 for obtaining light intensity measurements. As more clearly seen in FIGS. 2a and 2b, sample block 102 includes a plurality of predefined regions 110 in the form of openings, illustrated by way of example as generally circular, wherein the number of regions 110 correspond to the number of material samples that may be used with apparatus 100 at one time. Regions 110 are arranged in rows 112 equally spaced apart at a predetermined distance. Each region 110 extends from a top surface 114 to a bottom surface 116 of sample block 102 so as to completely extend through sample block 102. At top surface 114, regions 110 have a first diameter $d_1$, while at bottom surface 116, regions 110 have a second diameter $d_2$, wherein diameter $d_1 > d_2$ so as to form a ledge 118. Ledge 118 serves as a support for holding the bottom surfaces of vials (not shown) containing the material samples in the combinatorial library. Preferably, the vials are transparent to light of a predetermined wavelength, to be explained further in greater detail. The vials have a diameter that is slightly smaller than first diameter $d_1$ portion, but greater than second diameter $d_2$ portion such that the vials fit securely within regions 110. Further, the length of the first diameter d, portion is substantially greater than the length of the second diameter $d_2$ portion and approximately equal to the length of vials such that the vials are fully seated within regions 110 in sample block 102, thereby minimizing temperature variations throughout the vial, as detailed below. To enable easy removal of the vials, preferably an upper portion of the vials extend slightly above top surface 114 of sample block 102. Sample block 102 is constructed of aluminum or other suitable material.

Light source 104, which serves to provide at least one linearly polarized light beam, is positioned adjacent to the bottom surface 116 of sample block 102 such that light is directed to pass through at least one predefined region 110. Light source 104 may consist of one or more sources of unpolarized light in combination with a polarizing optical element, such as a light bulb and a sheet of polarizing film, or of a source of inherently polarized light, such as a laser or laser diode.

In one embodiment, light source 104 includes a plurality of light emitting diodes (LEDs), or other suitable light sources, such as lamps, that are adapted to simultaneously provide light beams having a narrow distribution of wavelengths. While the use of LEDs are preferred due to their low cost, low power consumption and the high intensity of the resulting light beam, it is understood that light source 104 need not be monochromatic. The use of other suitable light sources, such as lasers is also within the scope of this invention. However, if light source 104 only emits a single light beam and the illumination area covered by the light beam is less than the area of the array of material samples, an optical element, such as a fiber optic assembly, a combination of lenses, or a combination of lenses and mirrors must be used to divide the light beam among the material samples of the array, such that the entire array may be simultaneously illuminated.

Figure 3:
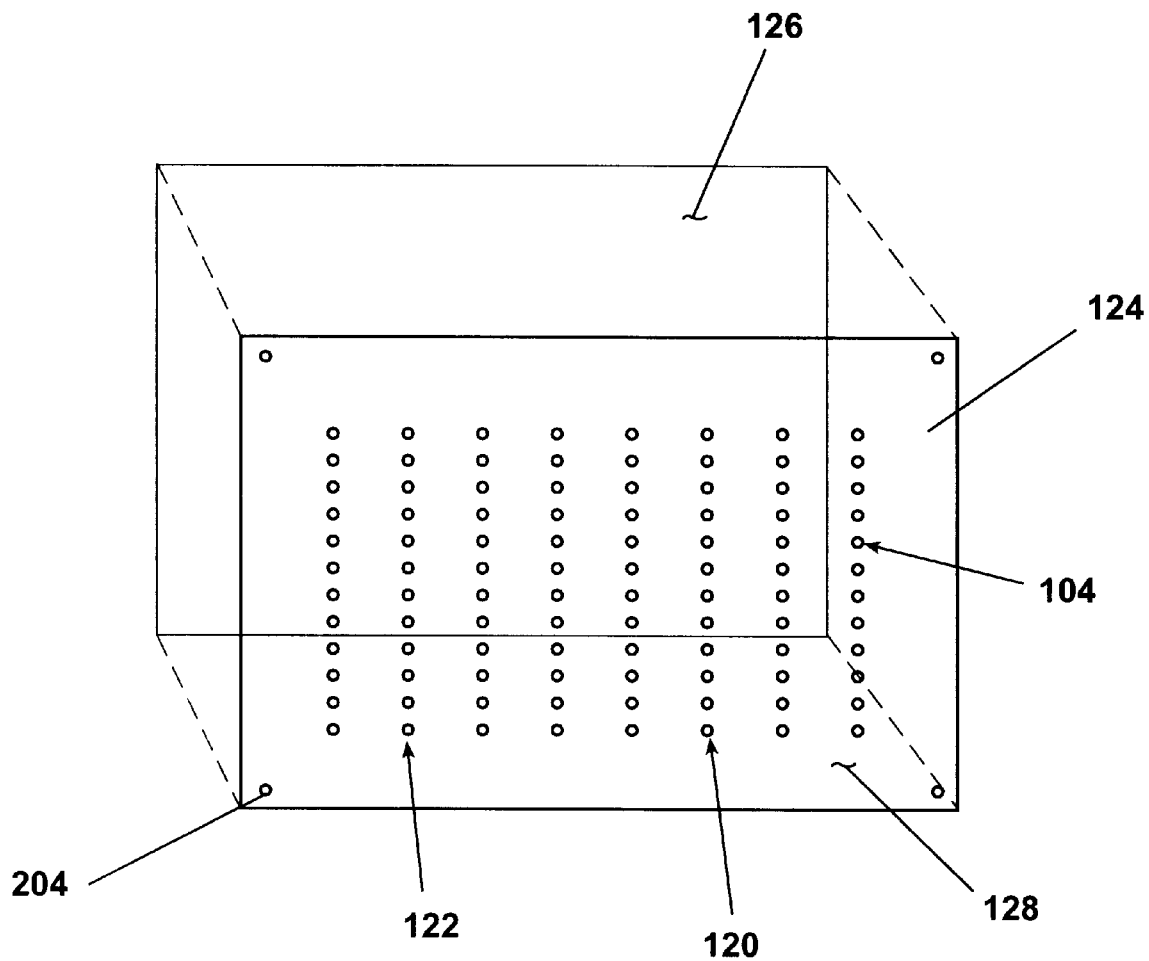
FIG. 3 is a perspective view of a light source support plate and a polarizer.

The LEDs are disposed in apertures 120 along rows 122 on a support plate 124, as seen in FIG. 3. Preferably, support plate 124 is constructed of plastic, to reduce manufacturing costs, although other suitable materials may be used. Further, support plate 124 is preferably a dark color, such as black, to reduce the occurrence of stray light scattering off support plate 124. Rows 122 correspond to rows 112 such that the LEDs are positioned so as to be substantially in alignment with regions 110, whereby the light beams are directed to pass simultaneously through the vials holding the material samples of the combinatorial library. To polarize the light beams emitted from the LEDs, a polarizing optical element ("polarizer") 126, is placed on a top surface 128 of support plate 124 containing the LEDs wherein polarizer 126 transmits only that portion of the light which has a specific linear polarization.

Alternatively, polarizer 126 may be a polarizing mirror (not shown). However, to incorporate a polarizing mirror into the apparatus, due to the angle at which the light beams must reflect from the mirror for polarization to occur (Brewster's angle), the relative positions of the light source, mirror, and sample block must be altered such that the reflected beam passes through the sample block.

Polarizer 126 polarizes the light beams before the light beams reach the vials of material samples, thus illuminating the material samples with focused linearly polarized light beams. The linearly polarized light beams have a predetermined wavelength that permits the light beams to pass through the vials and reach the material samples. As the polarized light beams are directed toward the material samples, they are partially collimated by their passage through apertures 120 of support plate 124 and apertures 110 in bottom surface 116 of sample block 102. Depending on the material samples' optical characteristics, which may be a function of factors such as composition or structure, the light beams are partially depolarized after passing through the material samples.

Figure 4A:
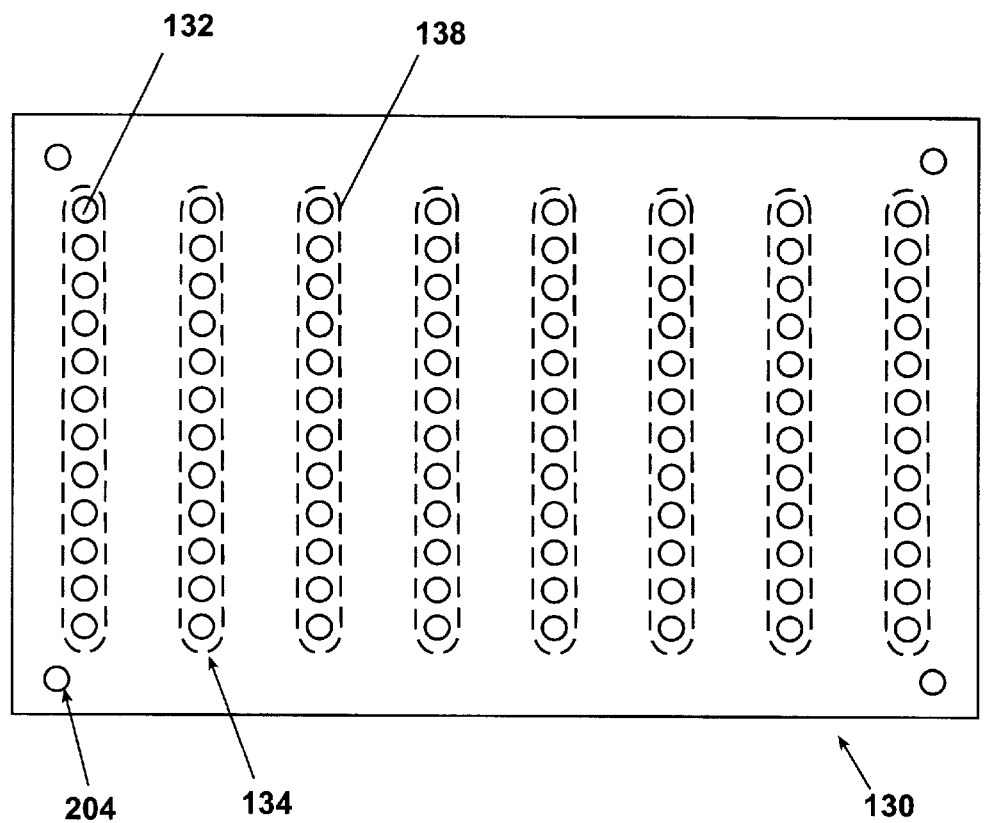
FIG. 4a is a top view of a collimator block.
Figure 4B:
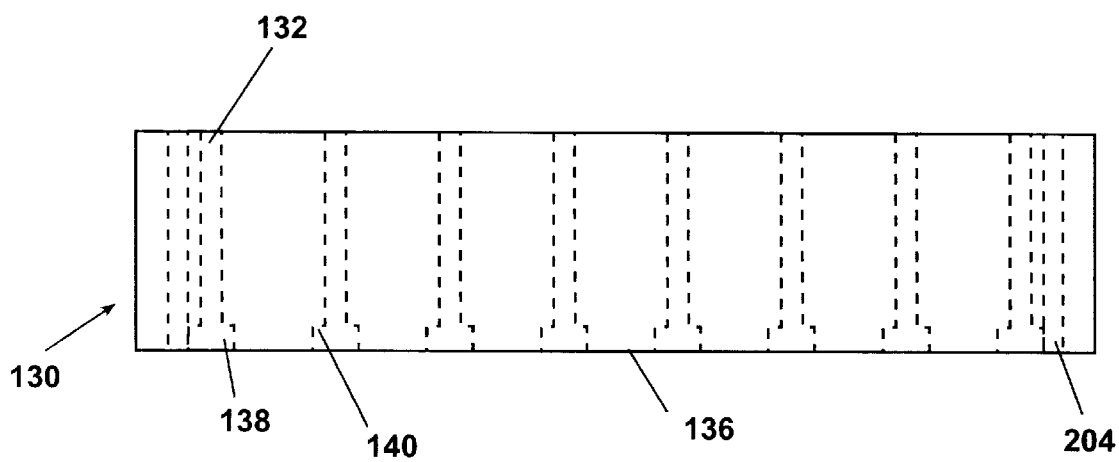

In accordance with one aspect of the invention, apparatus 100 further includes a collimator block 130, as seen in FIGS. 4a and 4b. Collimator block 130 is adapted to be placed on top surface 114 of sample block 102 to collimate the light beams that have passed through the material samples, thereby reducing the occurrence of stray light. Collimator block 130 includes a plurality of apertures 132 arranged in rows 134 defined in the block and extending therethrough, wherein the positioning of apertures 132 correspond to positioning of regions 110. A bottom surface 136 of collimator block 130 includes a plurality of trough sections 138. Trough sections 138 are formed along each row 134 and have a width that is greater than the diameter of apertures 132. Trough sections 138 are preferred to permit the vial tops to extend into collimator block 130, such that the collimator block rests on upper surface 114 of sample block 102, as opposed to the top portion of the vials, because walls of vials that are relatively thin may break under the weight of collimator block 130. Trough sections 138 further serve to aid in properly aligning the vials and apertures 132 of collimator block 130. The differences in the width and the diameter of apertures 132 and trough sections 138 result in a lip 140. Lip 140 improves the degree of collimation.

In accordance with another aspect of the invention, as shown in FIG. 1, a second sheet of linearly polarizing material ("analyzer") 142, such as a commercially available polarizing filter, is positioned adjacent top surface 114 of collimator block 130. Alternatively, a mirror may be positioned adjacent to the top surface 114 and so aligned that the light which passes through the collimator block 130 strikes the mirror surface at the polarizing angle (Brewster's angle). Preferably, analyzer 142 is spaced away from collimator block 130, which will be explained in further detail below. Analyzer 142 serves to block out any transmitted light beams that have the same polarization direction as the incident polarized light beams originating from light source 104, preferably allowing only depolarized light to pass through. For measurements of materials that undergo substantial changes in their optical characteristics, it is preferred that analyzer 142 has the polarization direction oriented at 90° with respect to polarizer 126, thereby, preferably resulting in complete blockage of the transmitted light if no depolarization occurs as the light beams pass through the samples. However, it is understood that apparatus 100 will still operate for other, non-zero relative orientations, such that some fraction of the incident light will be transmitted through analyzer 142 even in the absence of any depolarization.

Referring to FIG. 1, a detector 108 is positioned adjacent to analyzer 142 to capture the intensity readings from the depolarized scattered light beams and to output a signal corresponding to the intensity of the light beams as a function of time. In this manner, the intensity readings of the samples may be compared to ascertain specific desirable characteristics. Detector 108 can include one or more non-imaging optical sensors, such as semiconductor photodetectors or photomultipliers, or an imaging system such as the human eye, film or a charge-coupled device (CCD). In accordance with this aspect of the invention, the preferred detector 108 includes the CCD to capture all of the intensity readings of the material samples, as seen in FIG. 1. The CCD has a lens 144 that focuses the light as it enters detector 108. However, due to the narrow field of view of lens 144, to capture the intensity readings of the material samples simultaneously, detector 108 must be positioned a great distance from analyzer 108. As the distance between detector 108 and analyzer 108 is increased, the sensitivity of the readings captured by detector is decreased.

Figure 5:
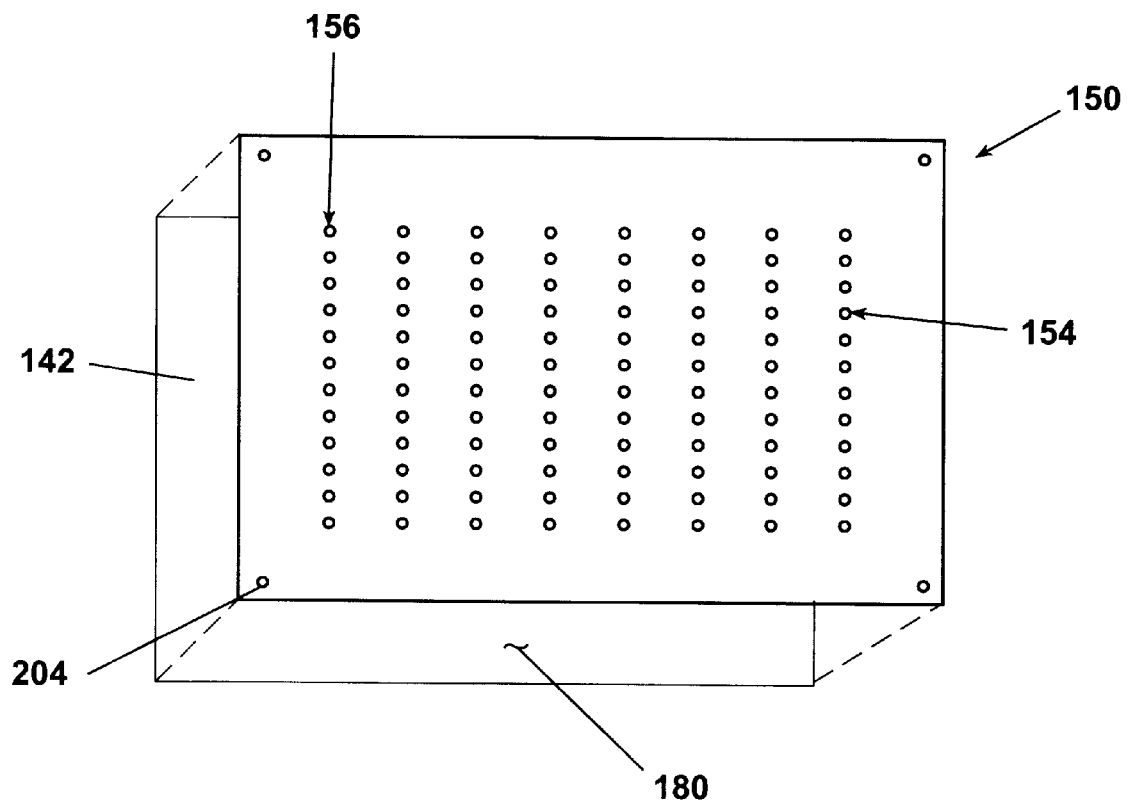
FIG. 5 is a perspective view of a first fiber optic plate and an analyzer.
Figure 6:
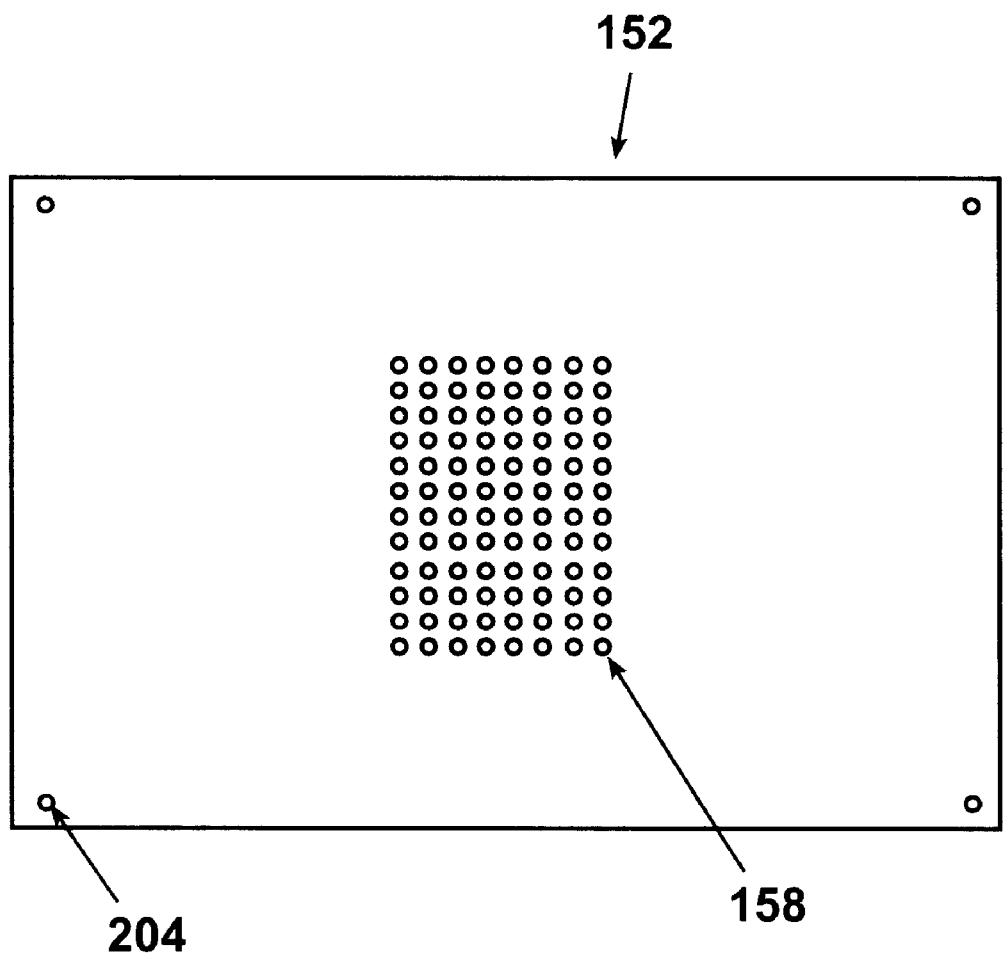
FIG. 6 is a top view of a second fiber optic plate.

Preferably, to reduce the dimensions of the region over which the light transmitted through the analyzer is distributed, detector 108 further includes an optical system such as fiber optic system 148. Fiber optic system 148 includes a first fiber optic plate 150, a second fiber optic plate 152 and fiber optic transmission media such as a plurality of fiber optic bundles (not shown). Preferably, fiber optic plates 150 and 152 are constructed of a dark plastic, preferably black, so as to be non-reflective and cost efficient to manufacture. As seen in FIG. 5, first fiber optic plate 150, which is positioned on a top surface of analyzer 142, includes an array of apertures 154 that are arranged a predetermined distance apart in rows 156 that correspond to rows 112 such that, in operation, the vials of material samples will be in substantial alignment with apertures 154. Second fiber optic plate 152, as seen in FIG. 6, also includes an array of apertures 158. Apertures 158 are arranged a predetermined distance apart so as to be closely packed together such that an overall dimension of the region of apertures 158 is reduced relative to the overall dimension of the region of apertures 154 of first fiber optic plate 150.

Positioned between first fiber optic plate 150 and second fiber optic plate 152 are the plurality of fiber optic bundles (not shown). The fiber optic bundles are connected at either end to the first and second fiber optic plates 150 and 152 at the respective holes 154, 156 and are in communication between first and second fiber optic plates 150 and 152. Fiber optic plates 150 and 152 cooperate with the fiber optic bundle to reduce the size of the area of transmitted light intensities, thereby enabling detector 108 to be positioned in close proximity with the remainder of apparatus 100, while permitting simultaneous scanning and characterizing of the entire array of material samples. Alternatively, a combination of lenses or a combination of lenses and mirrors may be used.

When the apparatus 100 is used to characterize material samples that produce only weak depolarization of an initially linearly polarized light beam it is preferred that apparatus 100 includes an optical filter 157 (shown in phantom in FIG. 1) such as a quarter-wave plate. Optical filter 157 is positioned between polarizer 126 and sample block 102, such that the linearly polarized light beams from light source 104 must pass through optical filter 157 prior to reaching the material samples in sample block 102. The optical filter 157 preferably converts linearly polarized light into circularly polarized light. When the circularly polarized light is transmitted through the material samples and analyzer 142, the intensity of the light beam is maximally dependent upon the optical characteristics of the material sample, thereby making it possible to detect very small changes in intensity for those materials that exhibit weak depolarization characteristics.

Screening Device for Effects of Temperature

Figure 7A:
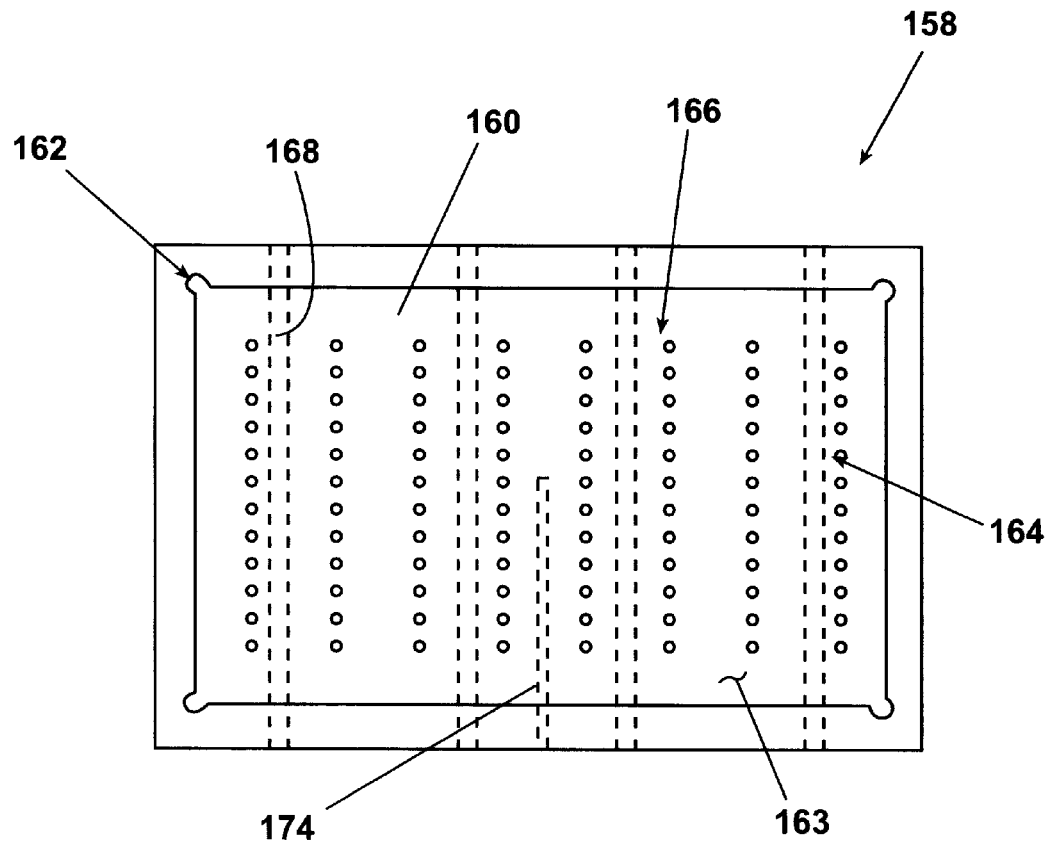
FIG. 7a is a top view of a temperature controlled block.
Figure 7B:
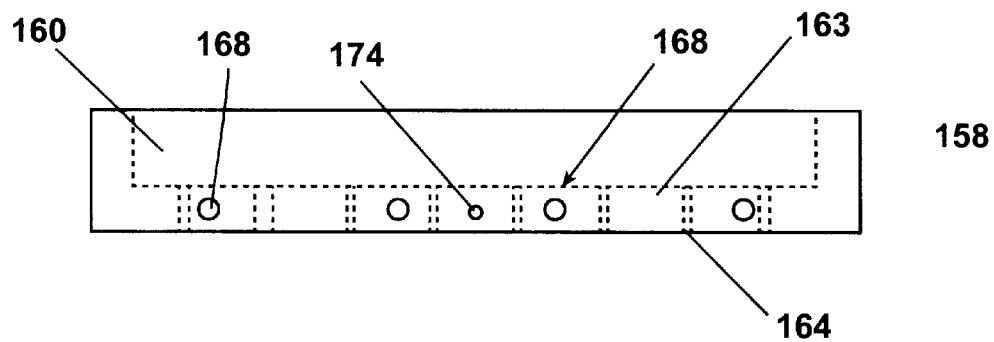

In accordance with another aspect of the invention, apparatus 100 may further include a temperature controlled block 159 positioned between polarizer 126 and analyzer 142. Block 159 can be adapted to heat or cool the array of material samples to achieve a desired result. For example, the block can be adapted to heat or cool during characterization such that detector 108 captures the intensity of the depolarized light beams and outputs a signal corresponding to the intensity of the light beams as a function of temperature, or as a function of time at a given temperature. In a preferred embodiment, block 159 is constructed of aluminum or other suitable material. Referring to FIGS. 7a and 7b, block 159 includes a well 160 having a size and shape that corresponds to the size and shape of sample block 102 such that sample block 102 may be positioned within well 160. Corners 162 of well 160 are preferably radiused so as to permit easy insertion of sample block 102 within well 160.

A bottom surface 163 of well 160 includes a plurality of apertures 164 that are arranged in rows 166, wherein the position of apertures 164 correspond to the positions of regions 110 in sample block 102 such that when sample block 102 is positioned in well 160, apertures 164 are in general alignment with regions 110 in sample block 102. Apertures 164 cooperate with support plate apertures 120 regions 110 in sample block 102 to collimate the linearly polarized light beams as they pass through support plate 124, sample block 102 and block 159. Block 159 is either anodized, if aluminum, or otherwise coated in black to render it substantially non-reflective, further reducing scattered light occurrence.

In a first embodiment, temperature controlled block 159 includes an array of channels 168 disposed below bottom surface 163 of well 160, between rows 166. Channels 168 extend laterally through block 159 and are adapted to receive resistance heaters or thermoelectric devices (not shown). Preferably, the temperature of the resistance heaters or thermoelectric devices is controlled by an external processor (not shown), although other suitable devices may be employed. The external processor monitors a signal from a monitoring device such as a thermocouple, thermistor or resistive thermal device (RTD) (not shown), positioned in a small channel 174 in approximately the center of block 159. The power supplied to the resistance heaters or thermoelectric devices is adjusted in response to the signal received from the monitoring device.

Figure 8A:
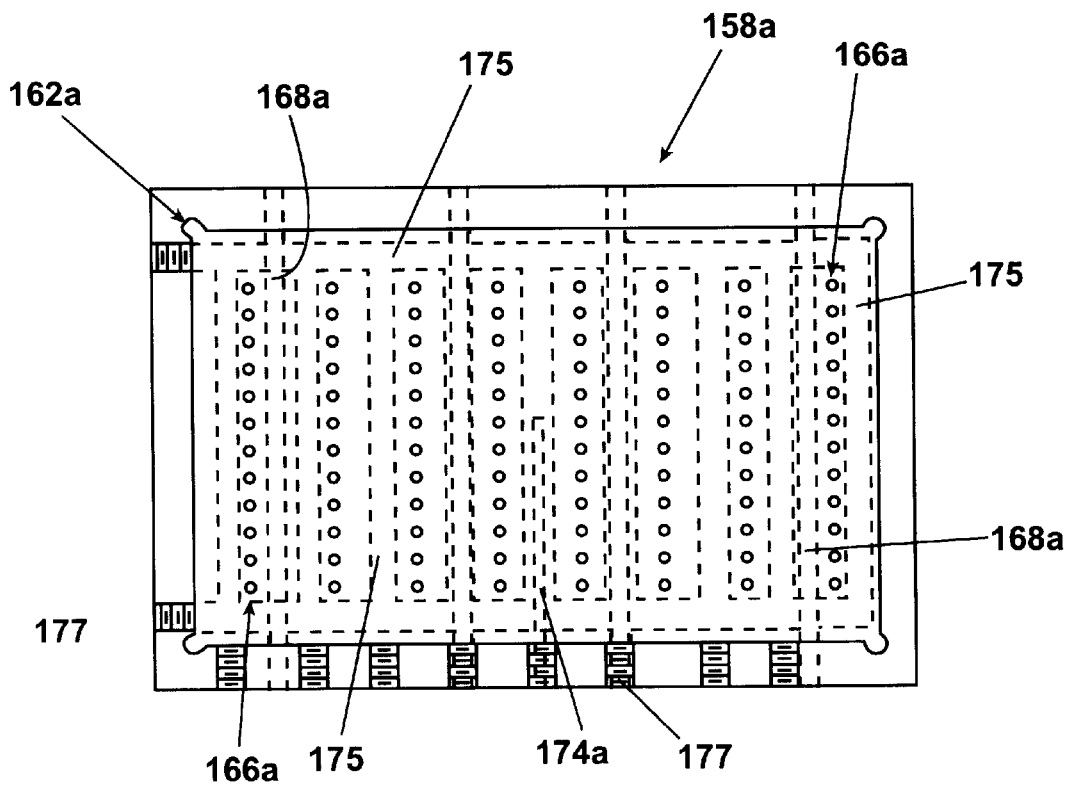
FIGS. 8a is a top view of an alternative embodiment of the temperature controlled block.
Figure 8B:
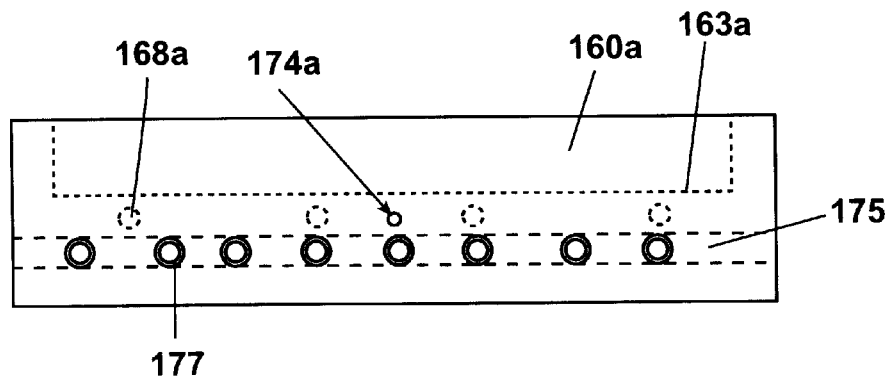

In another alternative embodiment, referring to FIGS. 8a and 8b, temperature-controlled block 159a may include both passages 175 carrying temperature agents and either channels 168a for resistance heaters or thermoelectric devices mounted to a surface of temperature controlled block 159a, wherein the temperature agents and resistance heaters or thermoelectric devices work in combination to vary the temperature of temperature-controlled block 159a. Similar to channels 168, passages 175 are disposed below bottom surface 163a of well 160a and between rows 166a. However, passages 175 are adapted to receive a liquid temperature agent (not shown) to vary the temperature of temperature controlled block 159a. Suitable temperature agents (which may be heated or cooled) include water, silicone oil or fluorinated solvent. Other suitable temperature agents may also be employed. In one embodiment, to ensure proper temperature control of temperature controlled block 159a, passages 175 extend both in a lateral and horizontal direction so as to extend around the perimeter of block 159a and between rows 166a. Entrance and exit ports 177 of the passages 175 are preferably threaded so as to permit easy assembly of tubing to a separate temperature agent reservoir.

In another embodiment, temperature controlled block 159a may include both channels 168a for resistance heaters and passages 175 carrying temperature agents working in combination to vary the temperature of temperature controlled block 159.

Screening Device for Effects of Pressure and Environment Composition

Figure 9:
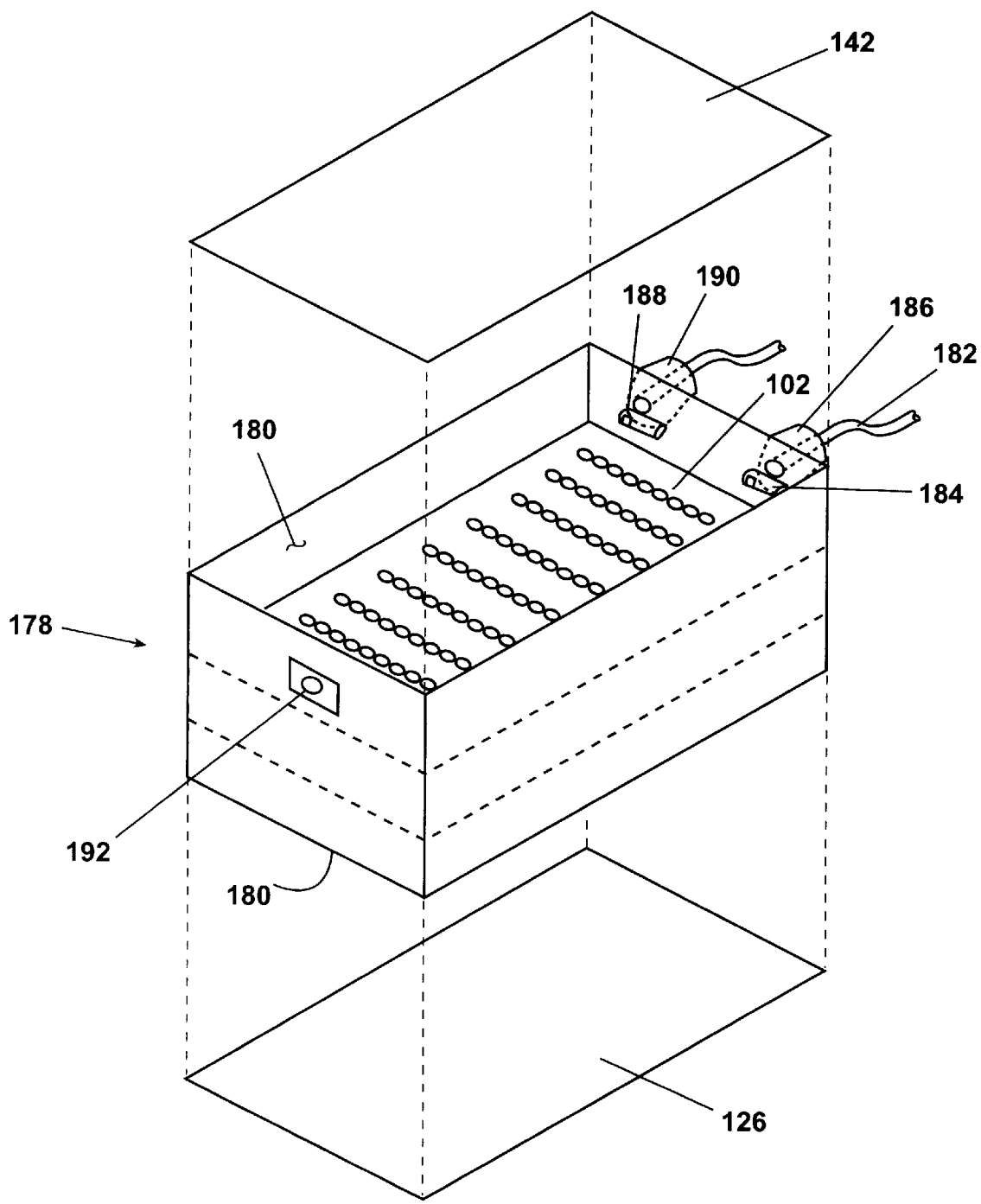
FIG. 9 is a schematic drawing of a substantially gas-tight environmental chamber with the sample block mounted therein.

Referring to FIG. 9, in accordance with another aspect of the invention, apparatus 100 may include at least one environmental chamber 178, preferably gas tight, positioned between polarizer 126 and analyzer 142. Sample block 102 is mounted within chamber 178. Both the upper and lower surfaces of chamber 178 are provided with optically transparent windows 180 to permit the light beams to reach the material samples within sample block 102 and pass through to analyzer 142. Chamber 178 is pressurized by at least one gas which is directed into chamber 178 through a conduit 182, or other suitable passageway. A pressure sensor 184 working in combination with an external processor (not shown) operates a servomechanically actuated regulator valve 186 or piston to control the pressure of substantially gas-tight environmental chamber 178. Detector 108 captures the depolarization data and outputs a signal corresponding to the data as a function of pressure, or of time at a given pressure.

In another embodiment, the chamber 178 is continuously filled with a mixture of two or more gases. In this embodiment, additional conduits 188 and servomechanically actuated regulator valves 190 are provided to control the flow of the gases into chamber 178. An external processor (not shown) serves to operate regulator valves 190. Alternatively, the gases may be mixed in a separate chamber (not shown), wherein the amounts of each gas being directed into the chamber is controlled by separate regulator valves. Once the gases are mixed they are then transported from the separate chamber via conduit 182 into chamber 178. A calibrated vent valve 192 is also included on chamber 178 to continuously permit a predetermined amount of the mixture to be vented from chamber 178. Detector 108, positioned on top of analyzer 142, captures depolarization data generated from the light beams passing through the material samples and analyzer and outputs a signal corresponding to the data as a function of gas composition, or of time at a specific gas composition.

In another embodiment, sample block 102 may be subdivided into a plurality of sealed zones (not shown), wherein each zone has at least one material sample disposed therein. Each zone would receive a separate gas, gas mixture, or pressure. Alternatively, each material sample may be sealed in a transparent vessel (not shown) wherein the pressure inside each vessel is changed by varying the temperature of the vessel.

Screening Device for Sensitivity of Electric Fields

Figure 10:
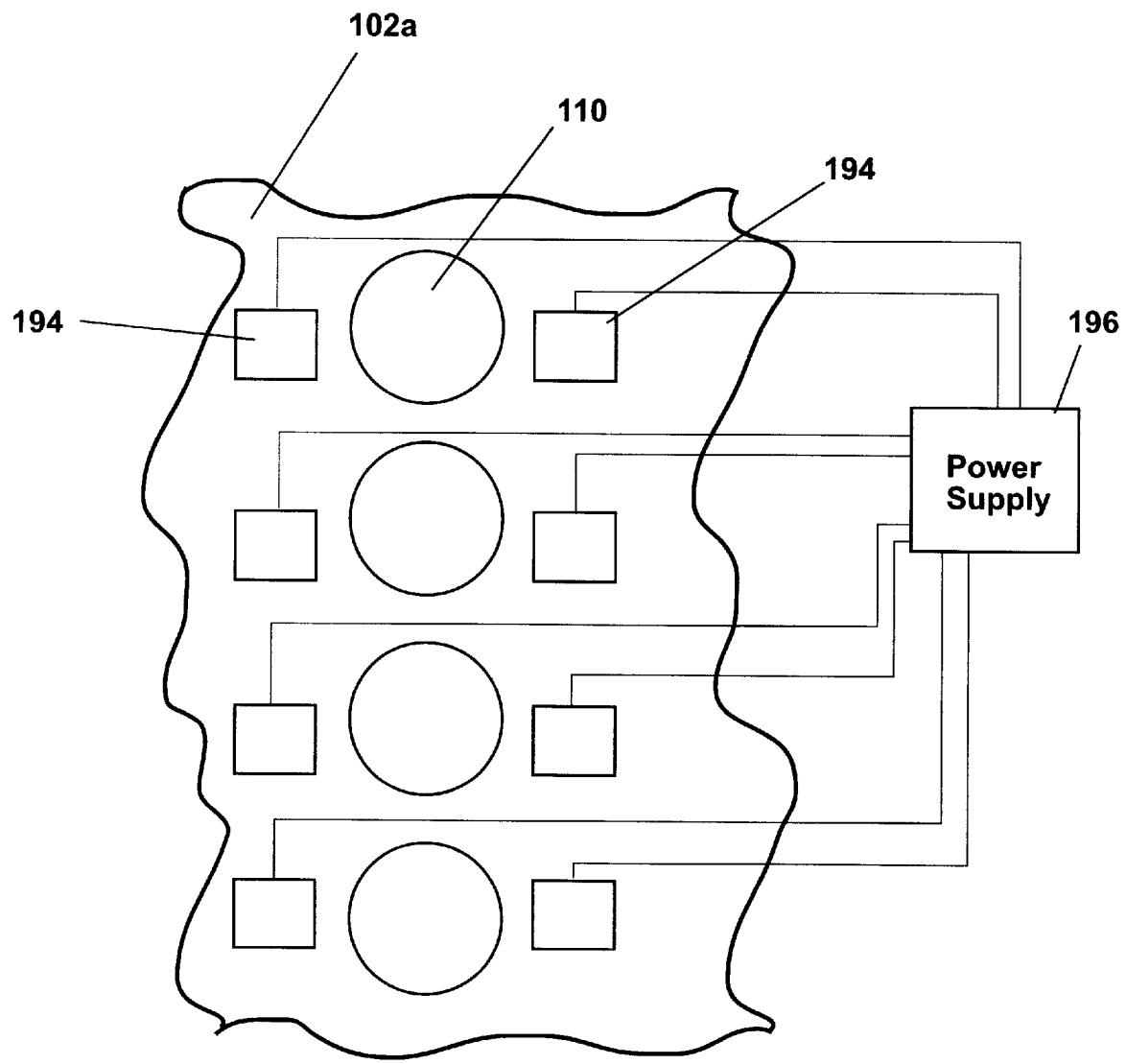
FIG. 10 is a cutaway of an alternative embodiment of the sample block having electrode pairs embedded therein.

In accordance with another aspect of the invention, FIG. 10 shows a cut-away portion of sample block 102a, where sample block 102a includes pairs of electrodes 194 embedded therein. Each pair of electrodes 194 are arranged in an opposing manner with a single region 110 positioned therebetween. Electrodes 194 are connected in parallel to a power supply 196, such that application of voltage across the pairs generates an electric field across each material sample. The electric field orients molecules or supramolecular assemblies within the material sample, thereby producing a change in the depolarization characteristics of the material samples. Detector 108 captures depolarization data of the material samples and outputs a signal corresponding to the data as a function of electric field strength, or as a function of time after the electric field is applied or removed, or as a function of the frequency of an alternating electric field.

When scanning the material samples as a function of voltage, preferably the sample block is a planar sheet of glass 102a upon which material samples are deposited. An array of electrode pairs is arranged on glass 102a to permit generation of high electric fields at only modest levels of applied voltage.

Screening Device for Sensitivity of Magnetic Fields

Figure 11A:
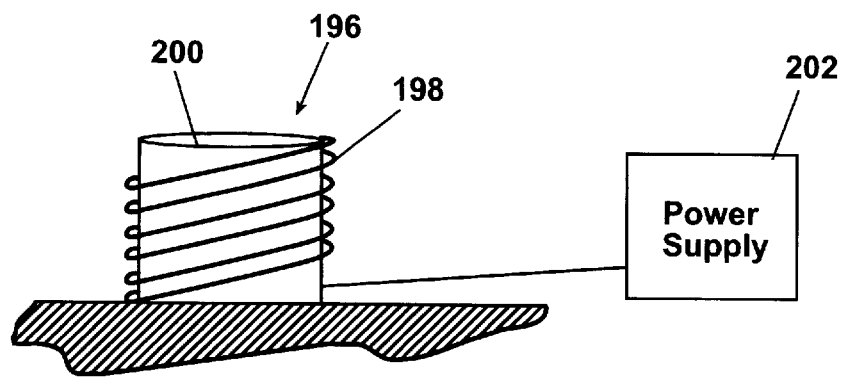
FIG. 11a is a schematic drawing of a solenoid device.

In accordance with another aspect of the invention, sample block 102b may further include a means of generating a magnetic field which surrounds each sample. In the preferred embodiment, sample block 102b further includes pairs of solenoids 197. Solenoids 197 are electromagnetic devices which generate a strong magnetic field when an electric current passes through them. As seen in FIG. 11a, solenoids 197 typically include a wire coil 198 wrapped around a solid core 200 made of a material having a high magnetic susceptibility such as soft iron.

Figure 11B:
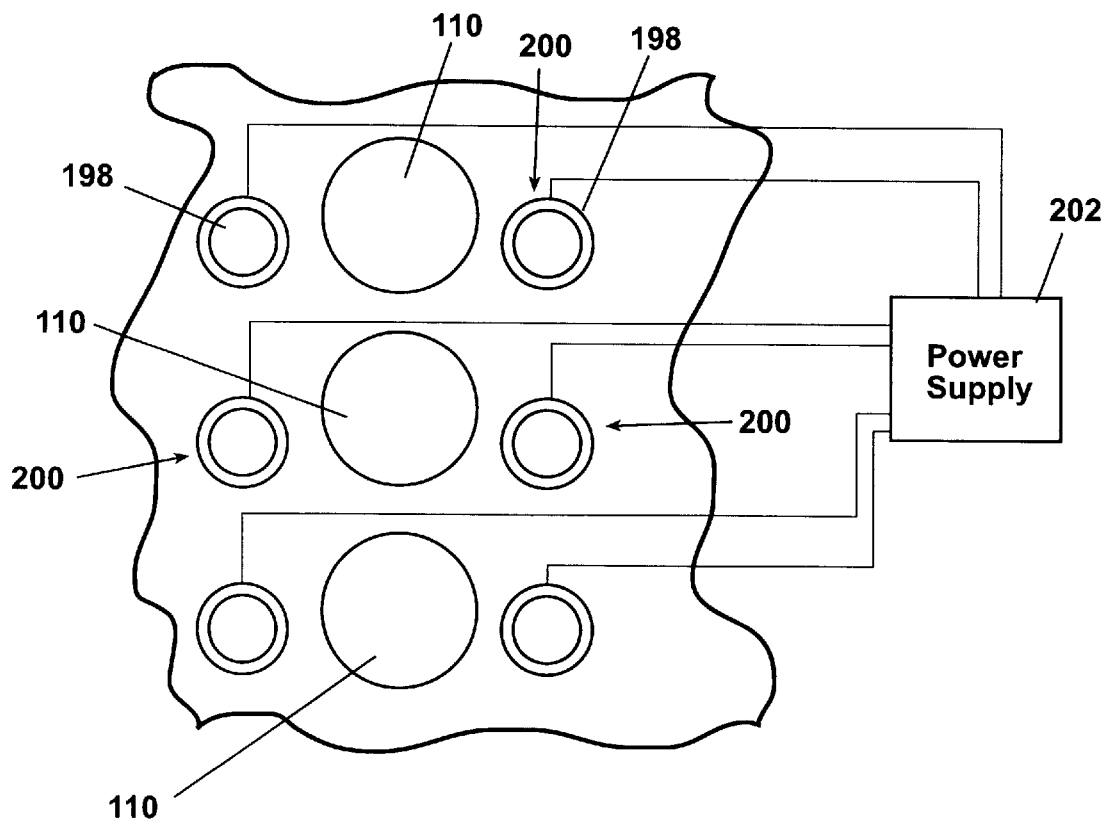
FIG. 11b is a cutaway of another embodiment of the sample block with pairs of the solenoid devices of FIG. 11 incorporated therein.

Referring to FIG. 11b, each solenoid pair 197 is arranged in an opposing manner with a single region 110 receiving a vial containing a material sample positioned therebetween. Solenoids 197 are connected in parallel to a power supply 202, such that application of an electric current across the pairs generate a magnetic field across each material sample. The magnetic field couples to the magnetic moment of molecules or supramolecular assemblies within the material sample, thereby orienting them with respect to the field and producing a change in the depolarizing characteristics of the material sample. Detector 108 captures depolarization data of the material samples and outputs a signal corresponding to the data as a function of magnetic field strength, or as a function of time after the magnetic field is applied or removed, or as a function of the frequency of an alternating magnetic field.

Figure 12:
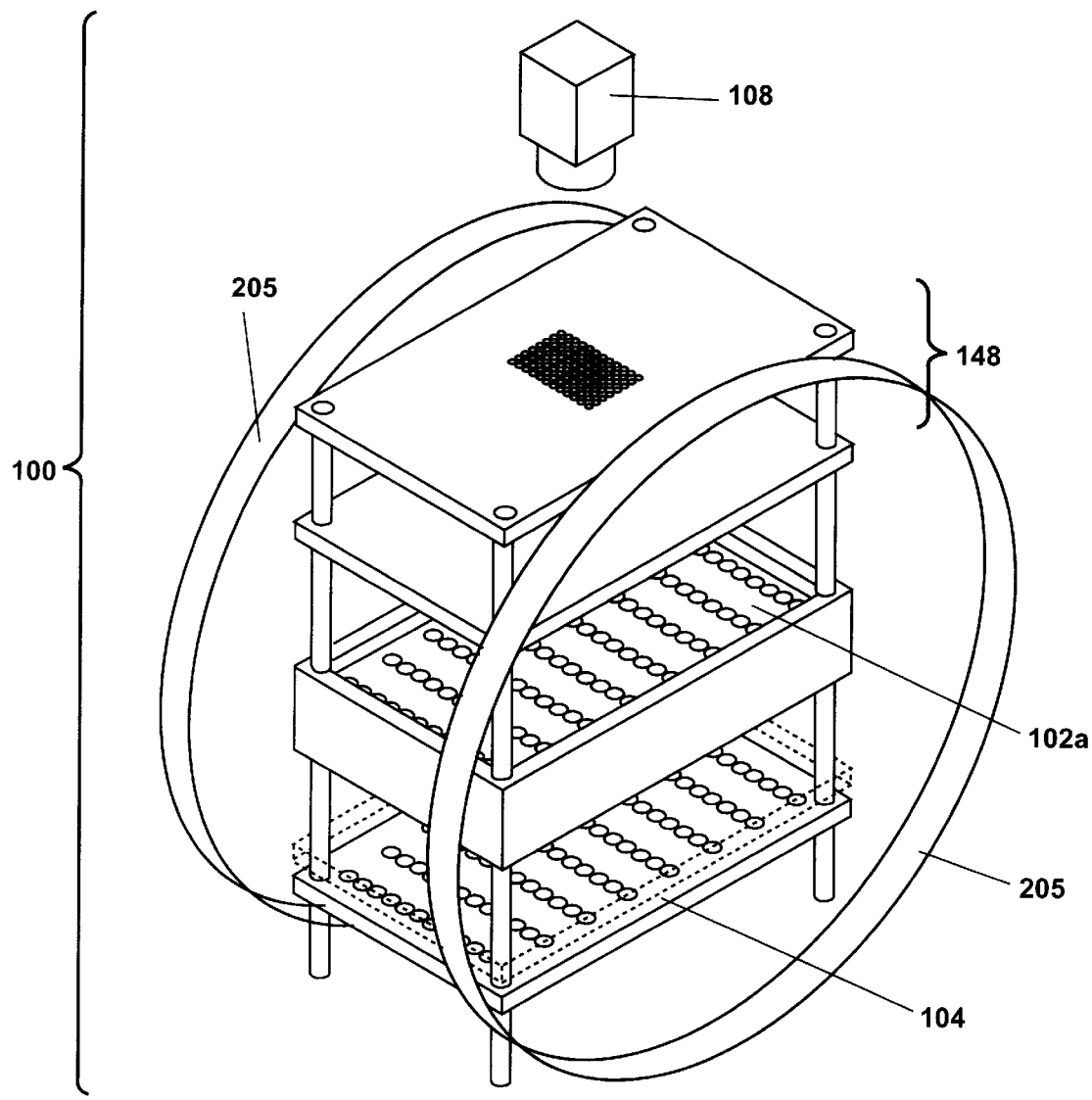
FIG. 12 is a schematic drawing of another embodiment of the apparatus incorporating a pair of circular wire coils.

Alternatively, the magnetic field may be generated by surrounding light source 104, polarizer 126, sample block 102a, analyzer 142 and fiber optic system 148 with a pair of circular wire coils 205 (i.e., Helmholz coils), as seen in FIG. 12, through which a current is passed. Wire coils 205 generate a relatively weak but spatially uniform magnetic field over the entire apparatus 100. In cases where it is desired to generate an extremely high magnetic field strength, apparatus 100 may be surrounded by one or more electromagnets (not shown). However, in both of these embodiments, the sample block must be constructed of a nonmagnetic (and preferably non-conducting, in order to facilitate measurements with alternating magnetic fields) material.

Assembly of Depolarized Scattering Light Array

Apparatus 100 is assembled so as to have all of the components arranged in series. As such, support plate 124, collimator block 130, first fiber optic plate 150 and second fiber optic plate 152 are all provided with connector holes 204 at their respective corners that are adapted to receive connector rods 206, as seen in FIG. 1. Starting with the bottom, apparatus 100 is assembled such that support plate 124 supporting light source 104 is in the first position with light source 104 simultaneously emitting a plurality of light beams upwardly in a linear direction to simultaneously illuminate the entire array of material samples. The polarizer 106 is placed on top surface 128 of support plate 124 to polarize the emitted light beams from light source 104.

Sample block 102, 102a or 102b, holding vials of material samples to be characterized in regions 110, is positioned above and in the path of the light beams emitted by light source 104 such that the polarized light beams are directed to pass through the material samples. Sample block 102 may be disposed in well 160 of temperature controlled block 159 and mounted in environmental chamber 178. Alternatively, sample block 102a or 102b is positioned alone above polarizer 106. In the preferred embodiment, sample block 102 is either anodized, if aluminum, or has a black outer surface to render it substantially non-reflective, thereby reducing scattered light occurrence. Next, collimator block 130 is placed on top surface 114 of sample block 102 to collimate the polarized light beams that are directed through the array of material samples. In one embodiment, collimator block 130 is constructed of polytetrafluoroethylene (e.g., TEFLON™), and painted black to reduced stray light from scattering inside the collimator block 130. TEFLON™ is preferred for its high melting temperature, thereby enabling collimator block 130 to rest directly on a heated vial block 102. Further, TEFLON™ is a poor thermal conductor, thereby keeping analyzer 142 from melting and losing its polarizing ability. Other plastics having similar characteristics, such as ployimide (e.g., without limitation, Kapton™), may be employed in a similar manner.

The analyzer 142, having a polarizing direction oriented, in one embodiment, at 90° to filter out any transmitted light that has the same polarization direction as the incident light beams, is placed above collimator block 130. Preferably analyzer 142 is spaced away from collimator block 130 a predetermined distance so as to produce an air gap between collimator block 130 and analyzer 142 when temperature controlled block 159, is used to heat vial block 102, as the heat would soften analyzer 142, causing loss of polarizing ability. The air gap may also serve as additional thermal insulation.

Next, first fiber optic plate 150 is placed on a top surface of analyzer 142 and second fiber optic plate 152 is placed spaced apart from and above first fiber optic plate 150. A plurality of fiber optic bundles are arranged in a tapered configuration between first fiber optic plate 150 and second fiber optic plate 152 to reduce the dimension of the area of transmitted light intensities. A detector 108, such as a CCD camera, is placed above second fiber optic plate 152 to simultaneously capture intensity readings from the entire array of material samples. Preferably, detector 108 is in communication with a data storage device (not shown) to permit analysis of the intensity readings.

Depolarized Scattering Method for Characterizing an Array of Materials

To screen and characterize the array of material samples, the material samples are provided in vials in regions 110 on sample block 102, 102a or are placed on a top surface of sample block 102b at regions 110. At least one material sample of the array is illuminated with a linearly polarized light beam having a predetermined wavelength. The vials in sample block 102, 102a, and sample block 102b are transparent to the predetermined wavelength of the light beam such that the light beam is permitted to pass through to the material sample. The light beam is modified after it passes through the material sample by passing the polarized light through an analyzer 142 that has a polarizing direction preferably oriented at 90° with respect to the polarizing direction of the linearly polarized light beam so as to completely filter out light intensities having the same polarization direction as the incident light beam. Next, changes in the intensity of the light beam due to changes in the optical characteristics of the material samples are detected and characteristics of the material sample are determined based on the intensity readings as a function of time.

In the preferred method, the step of illuminating the material sample includes providing a light source 104 that comprises a plurality of LEDs that simultaneously emit a plurality of light beams which are passed through a polarizer 126 so as to produce linearly polarized light beams. The linearly polarized light beams simultaneously illuminate the entire array of material samples. After the polarized light beams pass through the array, the beams are then collimated prior to being directed through the analyzer 142.

In an alternative method, the light beams are converted to circularly polarized light by passing the linearly polarized light beams through an optical filter 157 prior to reaching to material samples. The circularly polarized light permits scanning and characterizing of material samples that produce weakly polarized light beam intensities when subjected to linearly polarized light beams.

In accordance with another aspect of the invention, the detecting and determining step of the method includes collecting readings of the changes of light intensity of the light beams that pass through the array of material samples. After the intensity of the polarized light beams are filtered by the analyzer 142, the changes in intensity values are passed through a first fiber optic plate 150. Fiber optic bundles extending from first fiber optic plate 150 are connected to a second fiber optic plate 152 in a tapered configuration to reduce the area of transmitted light intensities such that intensity readings of the material samples may be captured simultaneously. A CCD camera is then provided to capture the intensity readings at predetermined time intervals, wherein the intensity readings provide information on the characteristics of the array of materials.

In accordance with another aspect of the invention, the method may further include the step of varying the temperature of the array of material samples at a predefined rate. This step is accomplished by placing sample block 102 into the temperature controlled block 159. As such, the determining step may be performed as a function of temperature or, alternatively, the material samples are heated or cooled to a fixed temperature and the changes in intensity are detected as a function of time.

In accordance with another aspect of the invention, the method may further include subjecting the material samples to pressure by enclosing the material sample in the environmental chamber 178 and filling chamber 178 with at least one gas. As such, the determining step may be performed as a function of pressure.

In accordance with another aspect of the invention, the method may further include continuously subjecting the material sample to a mixture to two or more gases. This step is accomplished by enclosing the material sample within the environmental chamber 178 and continuously filling the chamber 178 with the mixture of two or more gases. The mixture is vented from the chamber 178 at a predetermined rate. The determining step may be performed as a function of gas composition.

In accordance with another aspect of the invention, the method may further include the step of generating an electric field across each material sample. The electric field orients the molecular of the material samples or any supramolecular assemblies within the material samples, thereby changing the depolarization structure of the material samples. The determining step is then able to be performed as a function of electric field strength, as a function of time after the electric field is applied or removed, or as a function of the frequency of a alternating electric field.

In accordance with another aspect of the invention, the method may include the step of generating a magnetic field across each material sample. The magnetic field couples to the magnetic moment of molecules or supramolecular assemblies within the material sample, thereby orientating the assemblies with respect to the magenetic field and producing a change in the depolarizing characteristics of the material sample. The determining step is then able to be performed as a function of magnetic field strength.

EXAMPLE

The following example is intended as illustrative and non-limiting, and represent specific embodiments of the present invention.

Referring to FIGS. 13–18, to demonstrate depolarized scattering using an embodiment of the disclosed apparatus and method, the results of the characterization of a series of commercially available materials from Aldrich Chemical Company will be discussed. The materials consist of ethylene copolymerized with either methyl aerylate (MA) or vinyl acetate (VA) The characteristics of the copolymers, as reported by the supplier, appear below, in Table 1.

TABLE 1

| Melting Temperatures for Polyethylene Copolymers | | |
| --- | --- | --- |
| Region | Comonomer | Melting Point (° C.) |
| H4 | 12 wt % VA | 95 |
| G2 | 6.5 wt % MA | 106 |
| E2 | 18 wt % VA | 87 |
| D4 | 9 wt % MA | 93 |
| C2 | 25 wt % VA | 75 |

Approximately 60 mg of the copolymers are individually provided in flat-bottom glass vials 6 mm in inner diameter with wall thickness of 1 mm. At low temperatures, all of these materials exhibit a birefringent morphology that includes crystalline polyethylene domains in a matrix of ethylene and either vinyl acetate or methyl acrylate segments. Upon heating above the melting point of the cystalline domains, the sample forms a spatially isotropic liquid and the birefringence disappears.

Once the material samples are placed in the vials, the vials are heated on a hot plate to about 140° C. to eliminate birefringent stresses associated with processing the material samples. The resulting material, in liquid form, adopts the shape of the vials, thereby forming a uniform plug approximately 2 mm in height. The vials are then removed from the hot plate and cooled to room temperature.

Once cooled, the vials are placed in regions 110 in sample block 102 and sample block 102 is positioned within the temperature controlled block 159. The light source 104 is directed at the material samples. The temperature controlled block 159 is then heated from about 70 to 120° C. at a rate of about 1.0° C./min. The intensity of the depolarized light beams transmitted through the vials is captured every two minutes by a lens-coupled CCD camera using an exposure time of 15 ms.

Figures 13, 14:
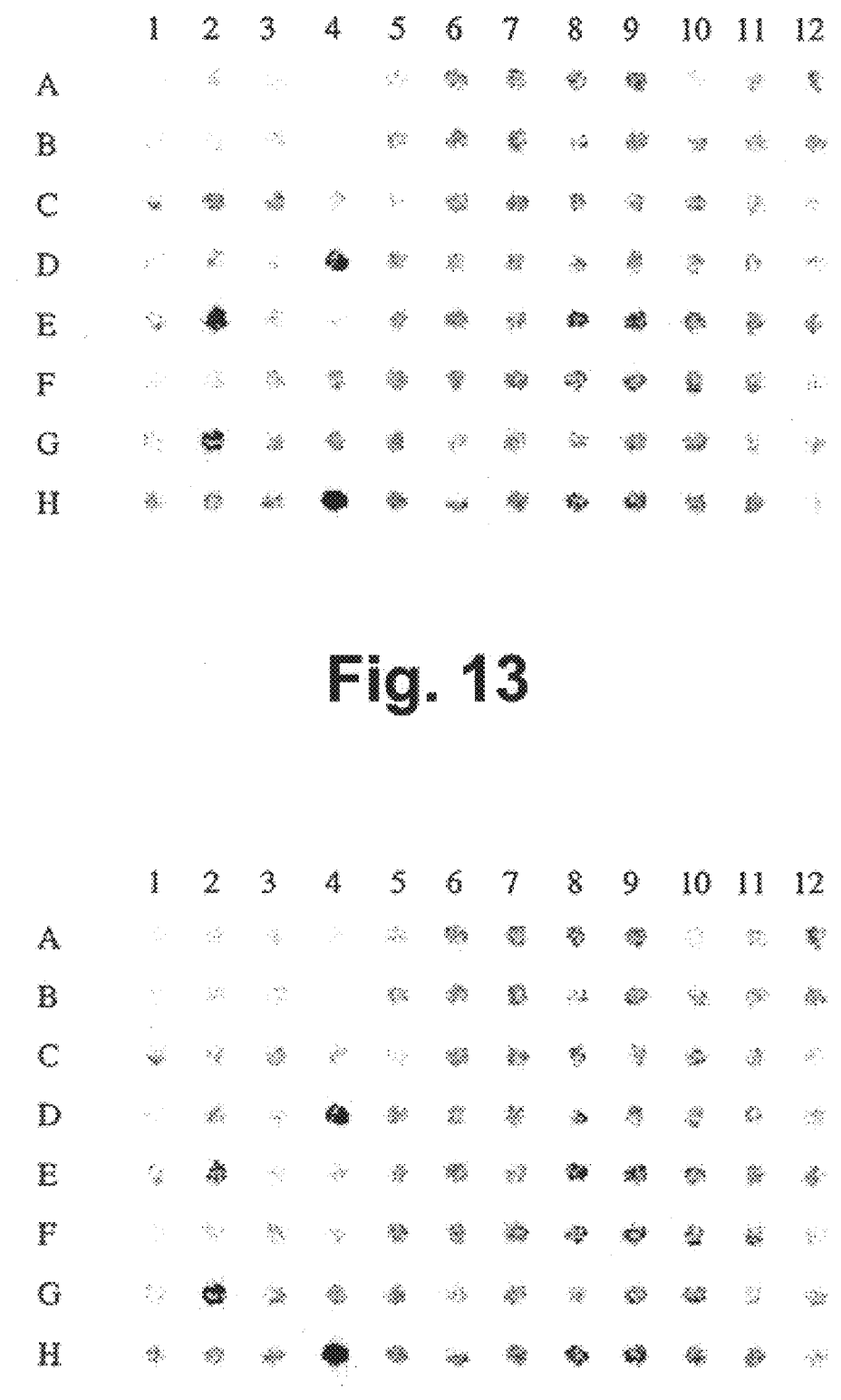

The resulting images captured by the CCD camera are shown in FIGS. 13–16. FIG. 13 is a negative image of the array of material samples at 70° C. with a linear grayscale. Regions B4, C2, D4, E2, F4, G2 and H4 contain samples. All other regions are empty.

FIG. 14 is a negative image recorded at about 86° C. upon heating at about 1 ° C/min. As can be seen, regions C2 and F2 show a marked drop in intensity relative to the 70° C. image.

Figures 15, 16:
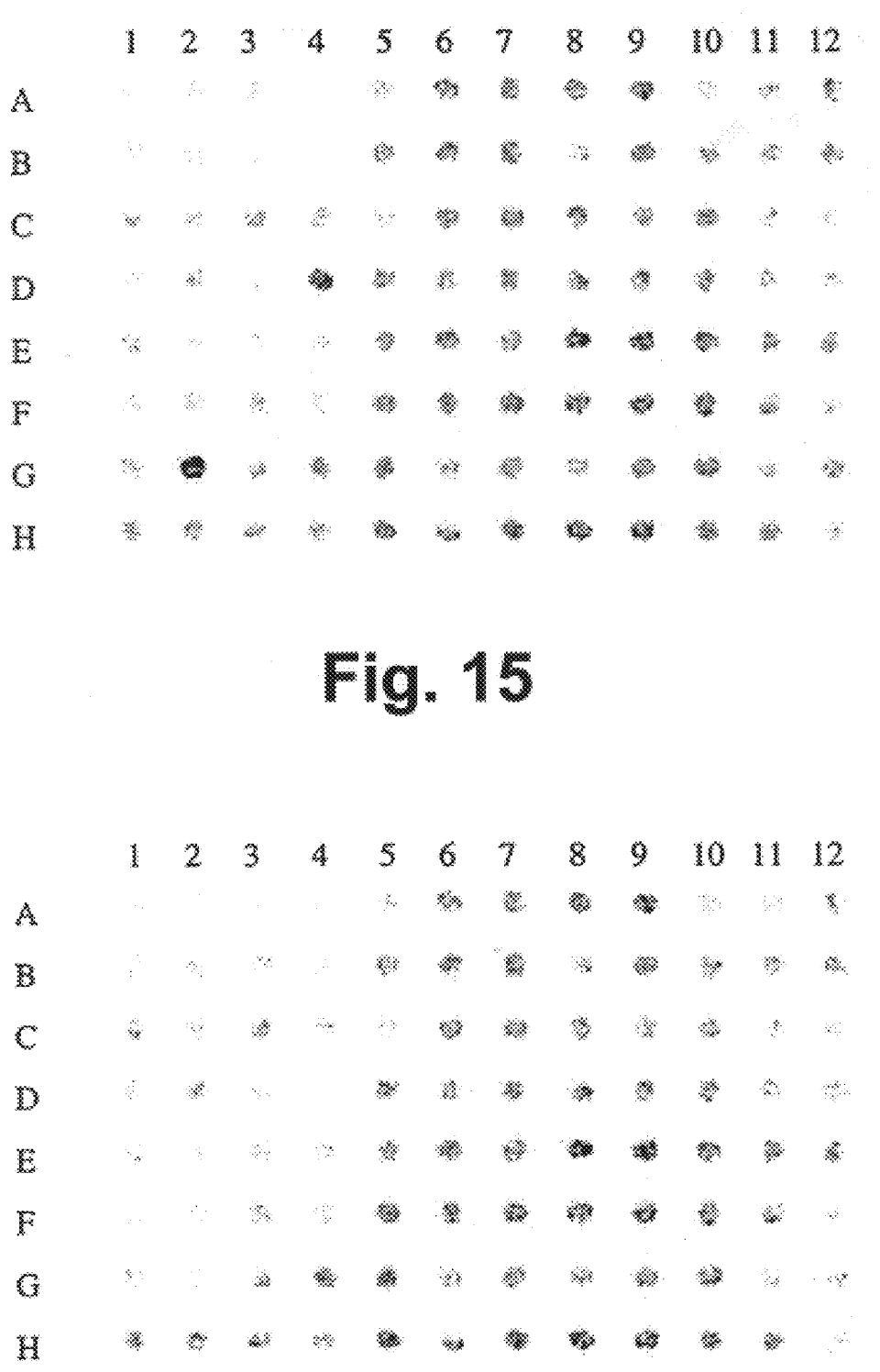

Referring to FIG. 15, at 102° C., only D4 and G2 exhibit a notable signal. However, upon reaching 116° C., all of the depolarization associated with the material samples has disappeared, indicating that all of the crystallites have melted, as can be seen in FIG. 16.

Figure 17:
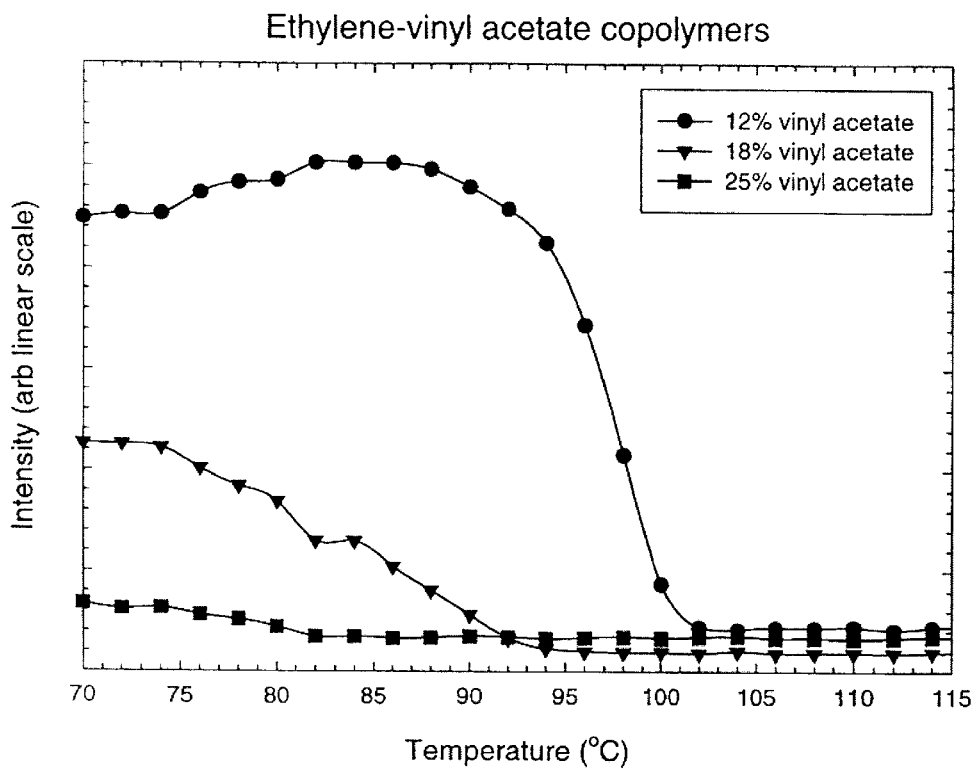
FIGS. 17–18 are graphical representations of the intensity readings of the array of materials as a function of temperature.

After the images of the material samples are captured by the CCD, the images can be digitized and analyzed, such as by suitable software. Graphical representations of the intensity data as a function of temperature are set out in FIGS. 17 and 18. Referring to FIG. 17, the temperature dependence of the transmitted intensity for regions G2 (6.5 wt % methyl acrylate) and D4 (9.0 wt % methyl acrylate) are shown. For comparison, the intensity data for empty region F2 is also shown. For the VA copolymers, the measured transition temperature for the 6.5 wt % material sample corresponds to the value supplied by the supplier, as seen in Table 1. However, the value for the 9 wt % material sample is approximately ten degrees less than the value reported in Table 1. This discrepency may reflect the presence of two different populations of cystallites. This hypothesis is supported by the differing slopes in the transition region (90–98° C. and 98–106° C., respectively).

Figure 18:
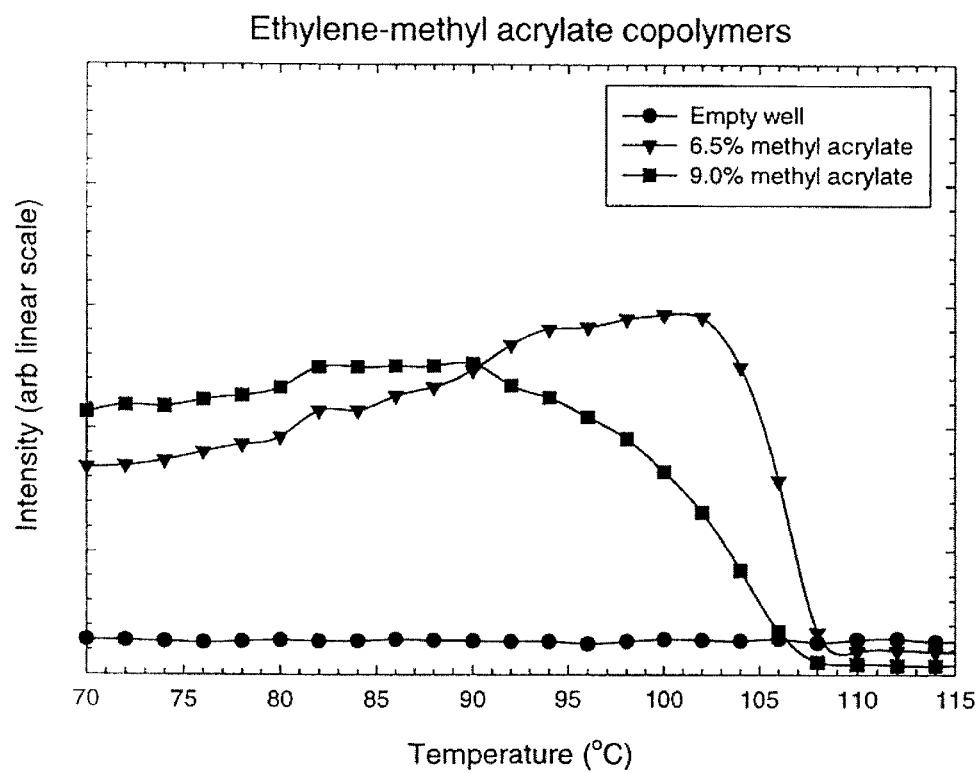

Referring to FIG. 18, the measured temperature dependence of the total intensity measured for regions H4 (12 wt % vinyl acetate), E2 (18 wt % vinyl acetate) and C2 (25 wt % vinyl acetate) of MA copolymers are depicted. The melting point is experimentally defined as the midpoint of the range in which the measured signal drops from the low-temperature value (approximated by a straight line) to the high-temperature value (also approximated by a straight line). Melting points identified in this manner generally correspond to the values reported by the supplier in Table 1, within a few degrees. This discrepancy is comparable to that associated with the thermal gradients within the system. Further, the discrepancy may also reflect the use of a different heating rate as compared to the supplier's heating rate.

Preferred embodiments of the present invention have been disclosed. A person of ordinary skill in the art would realize, however, that certain modifications would come within the teachings of this invention. Therefore, the following claims should be studied to determine the true scope and content of the invention.

What is claimed is:

1. An apparatus for characterizing an array of material samples in a library, comprising:
   a sample block adapted to receive a plurality of material samples to be characterized at predefined regions on said sample block;
   a light source for providing at least one linearly polarized light beam of a predetermined wavelength, said light source being positioned on a first side of said sample block such that said light beam may be directed to pass through at least one region and said material sample contained therein;
   an analyzer positioned on a second side of said sample block, said analyzer having a predetermined polarization direction different than said polarization direction of said linearly polarized light beam; and
   a detector for outputting a signal corresponding to a detected intensity of said light beam passing through said at least one material sample and said analyzer, said detector located adjacent said analyzer such that said analyzer is positioned between said detector and said sample block.

2. The apparatus of claim 1, further including an optical filter to convert said linearly polarized light beam into circularly polarized light, said optical filter being positioned on said first side of said sample block between said light source and said sample block.

3. The apparatus of claim 1, further including a collimator to collimate said polarized light beam, said collimator being positioned on a second side of said sample block between said sample block and said analyzer.

4. The apparatus of claim 1, further including a temperature controlled block having a plurality of holes through which said polarized light beams may pass, said sample block being positioned in said temperature controlled block such that said light beams are directed to pass through holes and through said predefined regions to said material samples.

5. The apparatus of claim 4, wherein the temperature of said temperature controlled block is varied by predetermined amounts by at least one resistance heater or a thermoelectric device.

6. The apparatus of claim 5, wherein the temperature of said temperature controlled block is monitored by a thermocouple, thermistor, or resistive thermal device.

7. The apparatus of claim 6, wherein a signal is outputted by said thermocouple, thermistor or resistive thermal device to an external processor, said external processor supplying power to said heater or said thermoelectric device in predetermined amounts so as to control the temperature of said temperature controlled block.

8. The apparatus of claim 4, wherein said temperature controlled block includes a plurality of passages formed therein, said passages receiving a temperature control agent to vary the temperature of said temperature controlled black by predetermined amounts.

9. The apparatus of claim 8, wherein said temperature control agent is water, silicone oil or fluorinated solvent.

10. The apparatus of claim 4, wherein said outputted signal corresponds to said intensity of said light beam as a function of temperature.

11. The apparatus of claim 1, further including a support plate for supporting said light source and a polarizer, wherein said polarizer is positioned between said light source and said sample block to provide said at least one linearly polarized light beam, said analyzer said predetermined polarization direction of said analyzer being different than a polarization direction of said polarizer.

12. The apparatus of claim 11, wherein said polarization direction of said analyzer is oriented 90 degrees with respect to said polarization direction of said polarizer.

13. The apparatus of claim 11, wherein said light source includes a plurality of individual light sources that are inserted into an array of corresponding apertures disposed in said support plate, said individual light sources simultaneously producing a plurality of light beams.

14. The apparatus of claim 13, wherein said detector simultaneously outputs a signal that corresponds to said detected intensity of all of said linearly polarized light beams passing through each material disposed in of said predefined regions and passing through said analyzer.

15. The apparatus of claim 14, further including an imaging system having a fiber optic system positioned adjacent to said analyzer to capture said light beams passing through said analyzer, said fiber optic system being in communication with said detector.

16. The apparatus of claim 15, wherein said fiber optic system includes: a first fiber optic plate positioned adjacent said analyzer, said first fiber optic plate having a first array of apertures arranged a predetermined distance apart so as to be in substantial alignment with said array of regions; and a second fiber optic plate positioned adjacent said first fiber optic plate, said second fiber optic plate having a second array of apertures arranged a predetermined distance apart such that said apertures in said second array are closely packed together relative to said first array of apertures of said first fiber optic plate, wherein said first fiber optic plate and said second fiber optic plate are connected together at said first and second arrays of apertures by a fiber optic bundle.

17. The apparatus of claim 1, wherein said outputted signal corresponds to said intensity of said light beam as a function of time.

18. The apparatus of claim 1, further including an environmental chamber having optically transparent windows to permit the passage of said light beam, wherein said sample block is mounted within said environmental chamber.

19. The apparatus of claim 18, wherein said environmental chamber is pressurized by at least one gas.

20. The apparatus of claim 19, wherein said environmental chamber further includes a pressure sensor for monitoring pressure in said environmental chamber, a regulator valve for controlling the pressure of said environmental chamber, and a processor for monitoring signals from said pressure sensor and for controlling the regulator valve so as to maintain the desired pressure inside said environmental chamber based on the signals received from said pressure sensor.

21. The apparatus of claim 20, wherein said outputted signal corresponds to said intensity of said light beam as a function of pressure.

22. The apparatus of claim 20, wherein said outputted signal corresponds to said intensity of said light beams as a function of time at a given pressure.

23. The apparatus of claim 18, wherein said environmental chamber is continuously filled with a mixture of two or more gases.

24. The apparatus of claim 23, wherein amounts of each of said gases are controlled by regulator valves.

25. The apparatus of claim 23, wherein said environmental chamber further includes a vent valve, wherein said vent valve continuously permits a predetermined amount of said mixture to be vented from said environmental chamber.

26. The apparatus of claim 23, wherein said outputted signal corresponds to said intensity of said light beam as a function of gas composition.

27. The apparatus of claim 23, wherein said outputted signal corresponds to said intensity of said light beams as a function of time at a given gas composition.

28. The apparatus of claim 1, wherein said sample block further includes pairs of electrodes embedded therein, wherein each pair of said electrodes is arranged in an opposing manner with one of said regions disposed therebetween.

29. The apparatus of claim 28, wherein each pair of electrodes are connected in parallel to a power supply such that application of a voltage across said pair generates an electric field extending across each of said regions.

30. The apparatus of claim 29, wherein said outputted signal corresponds to said intensity of said light beams as a function of applied voltage.

31. The apparatus of claim 29, wherein said outputted signal corresponds to said intensity of said light beams as a function of time after a given voltage is applied.

32. The apparatus of claim 29, wherein said outputted signal corresponds to said intensity of said light beams as a function of time after a given voltage is removed.

33. The apparatus of claim 1, wherein said sample block further includes pairs of solenoid devices embedded therein, wherein each of said pairs of solenoid devices are arranged in an opposing manner with a region disposed therebetween, so as to create a magnetic field extending across each of said regions.

34. The apparatus of claim 33, wherein said solenoid devices include circular coils wrapped around a solid metal core, wherein said coils are electrically connected to a power supply such that application of current across each of said circular coils generates said magnetic field extending across each of said regions.

35. The apparatus of claim 33, wherein said outputted signal corresponds to said detected intensity of said light beam as a function of magnetic field strength.

36. The apparatus of claim 33, wherein said outputted signal corresponds to said detected intensity of said light beam as a function of time after said magnetic field is applied.

37. The apparatus of claim 33, wherein said outputted signal corresponds to said intensity of said light beams as a function of time after said magnetic field is removed.

38. The apparatus of claim 1, further including a pair of circular wire coils connected to a power supply, wherein said wire coils are positioned adjacent to said apparatus in an opposing manner such that said apparatus is disposed therebetween so as to generate a uniform magnetic field over said apparatus.

39. The apparatus of claim 38, wherein said outputting signal corresponds to said detected intensity of said light beam as a function of magnetic field strength.

40. The apparatus of claim 38, wherein said outputted signal corresponds to said detected intensity of said light beam as a function of time after said magnetic field is applied.

41. The apparatus of claim 38, wherein said out putted signal corresponds to said detected intensity of said light beam as a function of time after said magnetic field is removed.

42. An apparatus for characterizing an array of material samples, comprising;
    a light source for providing at least one light beam, said light source being positioned in a support plate;
    a polarizer having a predetermined polarization direction, said polarizer positioned adjacent to said light source such that said light beam may be directed through said polarizer to produce a linearly polarized light beam;
    a temperature controlled block having a well with plurality of holes therethrough, said well adapted to receive a sample block having an array of predefined regions therein for containing the array of material samples, said linearly polarized light beam being directed through at least one of said holes of said well to pass through at least one of said regions in said sample block such that said linearly polarized light beam is directed at least one material sample;
    an analyzer positioned adjacent said temperature controlled block on a side opposite of said polarizer, said analyzer having a predetermined polarization direction that is different than a polarization direction of said polarizer; and
    a detector for outputting a signal corresponding to an intensity of said polarized light beam passing through said at least one material sample and said analyzer, said detector being located adjacent said analyzer on a side opposite said temperature controlled block such that said analyzer is positioned between said detector and said temperature controlled block.

43. The apparatus of claim 42, further including a collimator to collimate said polarized light beam, said collimator being positioned adjacent said temperature controlled block on a side opposite of said polarizer such that said collimator is positioned between said temperature controlled block and said analyzer.

44. The apparatus of claim 42, further including an optical filter to convert said linearly polarized light beam into a circularly polarized light beam, said optical filter being positioned on a first side of said temperature controlled block between said polarizer and said temperature controlled block.

45. The apparatus of claim 42, wherein the temperature of said temperature controlled block is varied by predetermined amounts by at least one resistance heater or a thermoelectric device.

46. The apparatus of claim 42, wherein said temperature controlled block includes a plurality of passages formed therein, said passages receiving a temperature control agent to vary the temperature of said temperature controlled block by predetermined amounts.

47. The apparatus of claim 46, wherein said temperature controlled block further includes resistance heaters or thermoelectric devices, such that said temperature agent and said resistance heaters or thermoelectric devices, in combination, serve to vary the temperature of said temperature controlled block by predetermined amounts.

48. The apparatus of claim 46, wherein said resistance heaters or thermoelectric devices are monitored by a thermocouple, a thermistor or resistive thermal device, said thermocouple, thermistor or resistive thermal device outputting a signal to an external processor which supplies power to said resistance heaters or thermoelectric devices in varying predetermined amounts so as to control the temperature of said temperature controlled block.

49. The apparatus of claim 42, wherein said polarization of said analyzer is oriented 90 degrees with respect to said predetermined polarization direction of said polarizer.

50. The apparatus of claim 42, wherein said light source produces a plurality of individual light beams that simultaneously illuminate all of said material samples of said array, and wherein said detector simultaneously outputs a signal corresponding to the detected intensity of said polarized light beams passing through each of said material samples and said analyzer.

51. The apparatus of claim 50 wherein said detector includes a fiber optic system to simultaneously capture said detected intensity of said plurality of light beams, said fiber optic system being positioned adjacent said analyzer and in communication with a charge-coupled device.

52. The apparatus of claim 50, wherein said outputted signal corresponds to said detected intensity of said polarized light beams as a function of time.

53. The apparatus of claim 50, wherein said outputted signal corresponds to said detected intensity of said polarized light beams as a function of temperature.

54. An apparatus for characterizing an array of material samples, comprising;
a light source providing at least one light beam, said light source being positioned in a support plate;
a polarizer having a predetermined polarization direction, said polarizer positioned adjacent to said light source such that said at least one light beam is directed through said first sheet of said polarizer to produce a linearly polarized light beam;
a substantially gas-tight environmental chamber having optically transparent windows to permit the passage of said linearly polarized light beam, wherein a sample block is mounted within said environmental chamber, said sample block having an array of predetermined regions therein for containing the array of material samples to be characterized, said linearly polarized light beam being directed through said windows and at least one region to illuminate at least one material sample;
an analyzer positioned adjacent to said environmental chamber on a side opposite of said polarizer, said analyzer having a polarization that is different than said predetermined polarization of said polarizer; and
a detector for outputting a signal corresponding to a detected intensity of said polarized light beam passing through said at least one material sample and said analyzer, said detector located adjacent said analyzer on a side opposite said environmental chamber such that said analyzer is positioned between said detector and said environmental chamber.

55. The apparatus of claim 54, wherein said environmental chamber is pressurized by at least one gas.

56. The apparatus of claim 54, wherein said environmental chamber is continuously filled with a mixture of at least two gases.

57. The apparatus of claim 56, wherein said environmental chamber further includes a vent valve, wherein said vent valve continuously permits a predetermined amount of said mixture to be vented from said environmental chamber.

58. The apparatus of claim 54, further including a collimator to collimate said polarized light beam, said collimator being positioned adjacent said environmental chamber on a side opposite said polarizer such that said collimator is positioned between said environmental chamber and said analyzer.

59. The apparatus of claim 54, further including an optical filter to convert said linearly polarized light beam into circularly polarized light, said optical filter being positioned on a first side of said environmental chamber between said polarizer and said environmental chamber.

60. The apparatus of claim 54, wherein said light source is a plurality of individual light sources that are inserted into an array of corresponding apertures disposed in said support plate, wherein said individual light sources simultaneously illuminate the array of material samples, and wherein said detector outputs a signal corresponding to said detected intensity of said polarized light beams passing through each of said material samples contained in said regions of said sample block and said analyzer.

61. The apparatus of claim 54, wherein said detector includes a fiber optic system to simultaneously capture said intensity of said plurality of light beams, wherein said fiber optic system includes:
a first fiber optic plate positioned adjacent to said analyzer, said first fiber optic plate having a first array of apertures arranged a predetermined distance apart so as to be in substantial alignment with said regions; and
a second fiber optic plate having a second array of apertures arranged a predetermined distance apart such that said apertures in said second array are closely packed together relative to said first array of apertures of said first fiber optic plate, wherein said first fiber optic plate and said second fiber optic plate are connected together by a fiber optic bundle.

62. An apparatus for characterizing an array of materials, comprising;
a light source for providing at least one light beam, said light source being positioned in a support plate;

a polarizer having a predetermined polarization direction, said polarizer positioned adjacent to said light source such that said light beam may be directed through said polarizer to produce a linearly polarized light beam;

a sample block having predefined regions for containing said array of material samples, wherein said sample block further includes pairs of solenoid devices embedded therein, wherein each of said pairs of solenoid devices are arranged in an opposing manner with one of said predefined regions disposed therebetween;

an analyzer positioned adjacent to said sample block on a side opposite of said polarizer, said analyzer having a polarization direction that is different than said predetermined polarization direction of said polarizer; and a detector for outputting a signal corresponding to a detected intensity of said polarized light beam passing through said at least one material sample contained in at least one region and said analyzer, said detector being located adjacent said analyzer on a side opposite said sample block such that said analyzer is positioned between said detector and said sample block.

63. The apparatus of claim 62, wherein said solenoid devices include circular coils wrapped around a solid metal core, wherein said coils are electrically connected to a power supply such that application of current across each of said circular coils generates a magnetic field extending across each of said regions.

64. The apparatus of claim 62, further including a collimator to collimate said polarized light beam, said collimator being positioned adjacent said sample block on a side opposite said polarizer such that said collimator is positioned between said sample block and said analyzer.

65. The apparatus of claim 62, wherein said light source is a plurality of individual light sources that are inserted into an array of corresponding apertures disposed in said support plate, wherein said individual light sources simultaneously illuminate the array of materials, and wherein said detector outputs a signal corresponding to said detected intensity of said polarized light beams passing through each of material samples contained in said regions of said sample block and said analyzer.

66. The apparatus of claim 62, wherein said detector includes a fiber optic system to simultaneously detect said intensity of said plurality of light beams, wherein said fiber optic system includes:

a first fiber optic plate positioned adjacent to said analyzer, said first fiber optic plate having a first array of apertures arranged a predetermined distance apart so as to be in substantial alignment with said array of regions; and a second fiber optic plate having a second array of apertures arranged a predetermined distance apart such that said apertures in said second array are closely packed together relative to said first array of apertures of said first fiber optic plate, wherein said first fiber optic plate and said second fiber optic plate are connected together by a fiber optic bundle.

67. The apparatus of claim 62, further including an optical filter to convert said linearly polarized light beam into circularly polarized light, said optical filter being positioned on said first side of said sample block between said polarizer and said sample block.

68. An apparatus for characterizing an array of material samples, comprising:

a light source for providing at least one light beam, said light source being positioned in a support plate;

a polarizer having a predetermined polarization direction, said polarizer positioned adjacent to said light source such that said light beam may be directed through said polarizer to produce a linearly polarized light beam;

a sample block having predefined regions therein for containing said array of material samples in said sample block, wherein said sample block further includes pairs of electrodes embedded therein, wherein each of said pairs of electrodes are arranged in an opposing manner with one of said regions disposed therebetween;

an analyzer positioned adjacent to said sample block on a side opposite of said polarizer, said analyzer having a polarization direction that is different than said predetermined polarization direction of said polarizer; and a detector for outputting a signal corresponding to a detected intensity of said polarized light beam passing through said at least one material sample contained in at least one of said predefined regions and said analyzer, said detector being located adjacent said analyzer on a side opposite said sample block such that said analyzer is positioned between said detector and said sample block.

69. The apparatus of claim 68, wherein said pairs of electrodes are connected in parallel to a power supply, such that application of a voltage across said pairs generates an electric field extending across each of said regions.

70. The apparatus of claim 68, further including a collimator to collimate said polarized light beam, said collimator being positioned adjacent said sample block on a side opposite said polarizer such that said collimator is positioned between said sample block and said analyzer.

71. The apparatus of claim 68, further including an optical filter to convert said linearly polarized light beam into circularly polarized light, said optical filter being positioned on said first side of said sample block between said polarizer and said sample block.

72. The apparatus of claim 68, wherein said light source is a plurality of individual light sources that are inserted into an array of corresponding apertures disposed in said support plate, wherein said individual light sources simultaneously illuminate the array of material samples, and wherein said detector outputs a signal corresponding to said detected intensity of said polarized light beams passing through each of said material samples contained in said predefined regions of said sample block and said analyzer.

73. The apparatus of claim 68, wherein said detector includes a fiber optic system to simultaneously detect said intensity of said plurality of light beams, wherein said fiber optic system includes:

a first fiber optic plate positioned adjacent to said analyzer, said first fiber optic plate having a first array of apertures arranged a predetermined distance apart so as to be in substantial alignment with said array of regions; and a second fiber optic plate having a second array of apertures arranged a predetermined distance apart such that said apertures in said second array are closely packed together relative to said first array of apertures of said first fiber optic plate, wherein said first fiber optic plate and said second fiber optic plate are connected together by a fiber optic bundle.

74. An apparatus for characterizing an array of material samples, comprising:

a light source for providing at least one light beam, said light source being positioned in a support plate;

a polarizer having a predetermined polarization direction, said polarizer positioned adjacent to said light source such that said light beam may be directed through said polarizer to produce a linearly polarized light beam;

a sample block having predefined region therein for containing said array of material samples in said sample block;

an analyzer positioned adjacent to said sample block on a side opposite of said polarizer, said analyzer having a polarization direction that is different than said predetermined polarization direction of said polarizer, wherein said light source, polarizer, sample block and analyzer are connected together as a single unit;

a detector for outputting a signal corresponding to a detected intensity of said polarized light beam passing through said at least one material sample contained in said predefined regions and said analyzer, said detector located adjacent said analyzer on a side opposite said sample block such that said sample block is positioned between said detector and said sample block; and a pair of circular coils positioned adjacent said single unit in an opposing manner with said single unit being disposed therebetween.

75. The apparatus of claim 74, wherein said circular coils are connected to a power supply, such that application of voltage across said pair of circular coils generates a uniform magnetic field across said single unit.

76. The apparatus of claim 75, wherein said single unit further includes a collimator to collimate said polarized light beam, said collimator being positioned adjacent said sample block on a side opposite said polarizer such that said collimator is positioned between said sample block and said analyzer.

77. The apparatus of claim 75, wherein said single unit further includes an optical filter being positioned on said first side of said sample block between said polarizer and said sample block.

78. The apparatus of claim 75, wherein said individual light sources simultaneously illuminate the array of material samples, and wherein said detector outputs a signal corresponding to said detected intensity of said polarized light beams passing through each of said material samples contained in said predefined regions of said sample block and said analyzer.

79. The apparatus of claim 75, wherein said unit further includes a fiber optic system to simultaneously detect said intensity of said plurality of light beams, wherein said fiber optic system includes:

a first fiber optic plate positioned adjacent to said analyzer, said first fiber optic plate having a first array of apertures arranged a predetermined distance apart so as to be in substantial alignment with said array of regions; and a second fiber optic plate having a second array of apertures arranged a predetermined distance apart such that said apertures in said second array are closely packed together relative to said first array of apertures of said first fiber optic plate, wherein said first fiber optic plate and said second fiber optic plate are connected together by a fiber optic bundle.

80. A method of characterizing an array of material samples, comprising the steps of:

providing an array of material samples disposed in regions spaced apart at a predetermined distance in a sample block containing;

illuminating at least one material sample of said array with at least one linearly polarized light beam passing through said region;

passing said linearly polarized light beam that has illuminated said at least one material sample through an analyzer that has a polarizing direction that is different than said polarization direction of said linearly polarized light beam;

detecting changes in intensity of said linearly polarized light beam after said light beam is passed though said material sample and said analyzer; and determining characteristics of said material sample based on said detected changes in said intensity of said light beam.

81. The method of claim 80, wherein said detecting step is performed at predefined intervals of time, and wherein said determining step determines said characteristics as a function of time.

82. The method of claim 80, further comprising the step of varying the temperature of said sample block at a predetermined rate; wherein said determining step determines said characteristics of said material samples as a function of temperature.

83. The method of claim 80, wherein said step of illuminating further comprises providing a light beam from a light source and polarizing said light beam by passing said light beam through a polarizer.

84. The method of claim 80, wherein said step of detecting further comprises collecting changes in said detected intensity and transmitting said changes to an imaging system.

85. The method of claim 80, wherein said step of illuminating further comprises simultaneously illuminating said array of material samples with a plurality of linearly polarized light beams, and wherein said characteristics of each of said material samples are determined simultaneously.

86. The method of claim 80, further including the step of collimating said linearly polarized light beam prior to step of passing said polarized light beam through said analyzer.

87. The method of claim 80, further including the step of converting said linearly polarized light into circularly polarized light prior to said illuminating step.

88. The method of claim 80, further comprising the step of subjecting the array of material samples to pressure by enclosing said array of materials in a substantially gas-tight environmental chamber and filling said environmental chamber with at least one gas.

89. The method of claim 88, wherein said step of pressurizing is performed at a predefined rate, wherein said determining step determines said characteristics as a function of pressure.

90. The method of claim 80, further comprising the step of subjecting the array of material samples to a mixture of two or more gases.

91. The method of claim 90, wherein said determining step determines said characteristics of said material sample as a function of gas composition.

92. The method of claim 80, further comprising the step of generating an electric field extending across each material sample disposed in each of said regions.

93. The method of claim 92, wherein said determining step determines said characteristics of said material sample as a function of electric field strength.

94. The method of claim 80, further comprising the step of generating a magnetic field extending across each material sample disposed in each of said regions.

95. The method of claim 94, wherein said determining step determines said characteristics of said material sample as a function of magnetic field strength.

96. The method of claim 80, further comprising the step of generating a substantially uniform magnetic field extending across the entire array of material samples.

97. The method of claim 80, wherein said step of detecting further comprises collecting changes in said intensity and transmitting said changes to a charge-coupled device.

98. The method of claim 80, wherein said providing step further requires that said array of material samples is composed of at least 10 material samples.

99. The method of claim 80, wherein said providing step further requires that said array of material samples is composed of at least 50 material samples.

100. The method of claim 80, wherein said providing step further requires that said array of material samples is composed of at least 100 material samples.

101. The method in claim 80, wherein the rates of said detecting step and determining steps equal a rate that is equal to or less than one minute per sample.

102. The method in claim 80, wherein detecting and determining steps are each performed at rates equal to or less than one minute per sample.

* * * * *